United States Patent
Gebreselassie et al.

(10) Patent No.: US 9,271,904 B2
(45) Date of Patent: *Mar. 1, 2016

(54) CONTROLLED RELEASE ORAL DELIVERY SYSTEMS

(75) Inventors: Petros Gebreselassie, Piscataway, NJ (US); Navroz Boghani, Flanders, NJ (US)

(73) Assignee: INTERCONTINENTAL GREAT BRANDS LLC, East Hanover, NJ (US)

( * ) Notice: Subject to any disclaimer, the term of this patent is extended or adjusted under 35 U.S.C. 154(b) by 2558 days.

This patent is subject to a terminal disclaimer.

(21) Appl. No.: 11/135,153

(22) Filed: May 23, 2005

(65) Prior Publication Data

US 2005/0260266 A1 Nov. 24, 2005

Related U.S. Application Data

(63) Continuation-in-part of application No. PCT/US2004/037185, filed on Nov. 22, 2004, and a continuation-in-part of application No. 11/083,968, filed on Mar. 21, 2005, now Pat. No. 8,828,423, said (Continued)

(51) Int. Cl.
*A23G 4/10* (2006.01)
*A23G 4/14* (2006.01)

(Continued)

(52) U.S. Cl.
CPC . *A61K 8/11* (2013.01); *A23G 4/064* (2013.01); *A23G 4/12* (2013.01); *A23G 4/20* (2013.01); *A23L 1/22025* (2013.01); *A61K 8/22* (2013.01);

(Continued)

(58) Field of Classification Search
CPC ............. A23G 4/10; A23G 4/14; A23G 4/02;
A23G 3/0017; A23G 3/346; A23G 3/38;
A23G 4/20; A23G 2220/20; A23G 2200/06;
A23G 2200/10; A61K 9/1635; A61K 9/149;
A61K 9/0056; A61K 9/145; A61K 9/1617;
A23L 1/22016; A23L 1/22025; A23V 2002/00

See application file for complete search history.

(56) References Cited

U.S. PATENT DOCUMENTS 1,633,336 A 6/1927 Larson
1,936,456 A 11/1933 Larson et al.

(Continued)

FOREIGN PATENT DOCUMENTS

CA 1 208 966 8/1986
CA 2 238 925 11/1999

(Continued)

OTHER PUBLICATIONS

Anonymous; "Caprol 3GO CAS No. 9007-48-1" XP002401201. Retrieved from the Internet: URL:http://www.abiteccorp.com/documents/3go-17_000.pdf (retrieved Sep. 28, 2006).

(Continued)

*Primary Examiner* — Trevor Love
(74) *Attorney, Agent, or Firm* — Cantor Colburn LLP

(57) ABSTRACT

Oral delivery systems including at least one encapsulated active are provided. The oral delivery systems include at least one active component; and a polymer matrix at least partially encapsulating the at least one active component. In some embodiments, the polymer matrix has a tensile strength of at least about 6,500 psi and/or includes at least one polymer having a water absorption of about 0.01% to about 50% by weight. The at least one active component may be an oral care active, which may be encapsulated alone or in combination with other actives, such as a taste masking active.

26 Claims, 1 Drawing Sheet

Related U.S. Application Data application No. PCT/US2004/037185 is a continuation-in-part of application No. 10/719,298, filed on Nov. 21, 2003, now abandoned, said application No. 11/083,968 is a continuation-in-part of application No. 10/719,298.

(51) Int. Cl.

| | | |
|---|---|---|
| *A61K 9/16* | (2006.01) | |
| *A23L 1/22* | (2006.01) | |
| *A61K 9/14* | (2006.01) | |
| *A61K 9/00* | (2006.01) | |
| *A23G 4/02* | (2006.01) | |
| *A23G 3/34* | (2006.01) | |
| *A61K 8/11* | (2006.01) | |
| *A23G 4/06* | (2006.01) | |
| *A23G 4/12* | (2006.01) | |
| *A23G 4/20* | (2006.01) | |
| *A61K 8/22* | (2006.01) | |
| *A61K 8/36* | (2006.01) | |
| *A61K 8/42* | (2006.01) | |
| *A61K 8/55* | (2006.01) | |
| *A61K 8/60* | (2006.01) | |
| *A61K 8/81* | (2006.01) | |
| *A61K 9/68* | (2006.01) | |
| *A61K 9/20* | (2006.01) | |
| *A61Q 11/00* | (2006.01) | |

(52) U.S. Cl.
CPC . *A61K 8/361* (2013.01); *A61K 8/42* (2013.01); *A61K 8/55* (2013.01); *A61K 8/602* (2013.01); *A61K 8/8135* (2013.01); *A61K 9/0058* (2013.01); *A61K 9/1617* (2013.01); *A61K 9/1623* (2013.01); *A61K 9/1635* (2013.01); *A61K 9/2081* (2013.01); *A61Q 11/00* (2013.01); *A61K 2800/412* (2013.01)

(56) References Cited

U.S. PATENT DOCUMENTS

| | | |
|---|---|---|
| 2,191,199 A | 2/1940 | Hall |
| 2,197,719 A | 4/1940 | Conner |
| 2,876,167 A | 3/1959 | Manahan |
| 2,886,440 A | 5/1959 | Kramer et al. |
| 2,886,441 A | 5/1959 | Kramer et al. |
| 2,886,442 A | 5/1959 | Kramer et al. |
| 2,886,443 A | 5/1959 | Rosenthal et al. |
| 2,886,444 A | 5/1959 | Rosenthal et al. |
| 2,886,445 A | 5/1959 | Rosenthal et al. |
| 2,886,446 A | 5/1959 | Kramer et al. |
| 2,886,449 A | 5/1959 | Rosenthal et al. |
| 3,004,897 A | 10/1961 | Shore |
| 3,052,552 A | 9/1962 | Koerner et al. |
| 3,117,027 A | 1/1964 | Lindlof et al. |
| 3,124,459 A | 3/1964 | Erwin |
| 3,159,585 A | 12/1964 | Evans et al. |
| 3,241,520 A | 3/1966 | Wurster et al. |
| 3,341,416 A | 9/1967 | Anderson et al. |
| 3,475,533 A | 10/1969 | Mayrand |
| 3,538,230 A | 11/1970 | Pader et al. |
| 3,664,962 A | 5/1972 | Kelly et al. |
| 3,664,963 A | 5/1972 | Pasin |
| 3,677,771 A | 7/1972 | Kolar, Jr. |
| 3,691,090 A | 9/1972 | Kitajima et al. |
| 3,795,744 A | 3/1974 | Ogawa et al. |
| 3,819,838 A | 6/1974 | Smith et al. |
| 3,821,417 A | 6/1974 | Westall et al. |
| 3,826,847 A | 7/1974 | Ogawa et al. |
| 3,857,964 A | 12/1974 | Yolles |
| 3,862,307 A | 1/1975 | Di Giulio |
| 3,872,021 A | 3/1975 | McKnight |
| 3,878,938 A | 4/1975 | Venables et al. |
| 3,912,817 A | 10/1975 | Sapsowitz |
| 3,930,026 A | 12/1975 | Clark |
| 3,943,258 A | 3/1976 | Bahoshy et al. |
| 3,962,416 A | 6/1976 | Katzen |
| 3,962,463 A | 6/1976 | Witzel |
| 3,974,293 A | 8/1976 | Witzel |
| 3,984,574 A | 10/1976 | Comollo |
| 4,037,000 A | 7/1977 | Burge et al. |
| 4,045,581 A | 8/1977 | Mackay et al. |
| 4,083,995 A | 4/1978 | Mitchell et al. |
| 4,107,360 A | 8/1978 | Schmidgall |
| 4,130,638 A | 12/1978 | Dhabhar et al. |
| 4,136,163 A | 1/1979 | Watson et al. |
| 4,139,639 A | 2/1979 | Bahoshy et al. |
| 4,148,872 A | 4/1979 | Wagenknecht et al. |
| 4,150,112 A | 4/1979 | Wagenknecht et al. |
| 4,156,715 A | 5/1979 | Wagenknecht et al. |
| 4,156,716 A | 5/1979 | Wagenknecht et al. |
| 4,157,385 A | 6/1979 | Wagenknecht et al. |
| 4,159,315 A | 6/1979 | Wagenknecht et al. |
| 4,160,054 A | 7/1979 | Wagenknecht et al. |
| 4,160,820 A | 7/1979 | Wagenknecht et al. |
| 4,187,320 A | 2/1980 | Koch et al. |
| 4,208,431 A | 6/1980 | Friello et al. |
| 4,217,368 A | 8/1980 | Witzel et al. |
| 4,224,345 A | 9/1980 | Tezuka et al. |
| 4,230,688 A | 10/1980 | Rowsell et al. |
| 4,271,199 A | 6/1981 | Cherukuri et al. |
| 4,276,312 A | 6/1981 | Merritt |
| 4,295,845 A | 10/1981 | Sepulveda et al. |
| 4,314,990 A | 2/1982 | Denny, Jr. et al. |
| 4,340,583 A | 7/1982 | Wason |
| 4,352,823 A | 10/1982 | Cherukuri et al. |
| 4,352,825 A | 10/1982 | Cherukuri et al. |
| 4,363,756 A | 12/1982 | Sepulveda et al. |
| 4,370,350 A * | 1/1983 | Fisher et al. ................ 426/5 |
| 4,384,004 A | 5/1983 | Cea et al. |
| 4,386,106 A | 5/1983 | Merritt et al. |
| 4,452,821 A | 6/1984 | Gergely |
| 4,457,857 A | 7/1984 | Sepulveda et al. |
| 4,459,425 A | 7/1984 | Amano et al. |
| 4,485,118 A | 11/1984 | Carroll et al. |
| 4,513,012 A | 4/1985 | Carroll et al. |
| 4,515,769 A | 5/1985 | Merritt et al. |
| 4,585,649 A | 4/1986 | Lynch |
| 4,590,075 A | 5/1986 | Wei et al. |
| 4,597,970 A | 7/1986 | Sharma et al. |
| 4,614,649 A | 9/1986 | Gorman et al. |
| 4,614,654 A | 9/1986 | Ream et al. |
| 4,627,987 A | 12/1986 | Barnett et al. |
| 4,634,593 A | 1/1987 | Stroz et al. |
| 4,673,577 A | 6/1987 | Patel |
| 4,711,784 A | 12/1987 | Yang |
| 4,722,845 A | 2/1988 | Cherukuri et al. |
| 4,726,953 A | 2/1988 | Carroll et al. |
| 4,740,376 A * | 4/1988 | Yang ................ 426/5 |
| 4,741,905 A | 5/1988 | Huzinec |
| 4,749,575 A | 6/1988 | Rotman |
| 4,751,095 A | 6/1988 | Karl et al. |
| 4,752,481 A | 6/1988 | Dokuzovic |
| 4,753,790 A | 6/1988 | Silva et al. |
| 4,764,382 A | 8/1988 | Kydonieus et al. |
| 4,771,784 A | 9/1988 | Kozin et al. |
| 4,800,087 A | 1/1989 | Mehta |
| 4,804,548 A | 2/1989 | Sharma et al. |
| 4,816,265 A | 3/1989 | Cherukuri et al. |
| 4,822,599 A | 4/1989 | Mitra |
| 4,824,681 A | 4/1989 | Schobel et al. |
| 4,828,845 A | 5/1989 | Zamudio-Tena et al. |
| 4,828,857 A | 5/1989 | Sharma et al. |
| 4,842,762 A | 6/1989 | Sabol, Jr. et al. |
| 4,871,570 A | 10/1989 | Barnett et al. |
| 4,904,482 A | 2/1990 | Patel et al. |
| 4,911,934 A | 3/1990 | Yang et al. |
| 4,915,958 A | 4/1990 | Faust et al. |
| 4,918,182 A | 4/1990 | Jackson et al. |
| 4,919,841 A | 4/1990 | Kamel et al. |
| 4,923,684 A | 5/1990 | Ibrahim et al. |

(56) References Cited

U.S. PATENT DOCUMENTS

| | | |
|---|---|---|
| 4,927,646 A | 5/1990 | Jenner et al. |
| 4,929,447 A | 5/1990 | Yang |
| 4,931,293 A | 6/1990 | Cherukuri et al. |
| 4,933,190 A | 6/1990 | Cherukuri et al. |
| 4,952,407 A | 8/1990 | Record et al. |
| 4,971,797 A | 11/1990 | Cherukuri et al. |
| 4,971,806 A | 11/1990 | Cherukuri |
| 4,978,537 A | 12/1990 | Song |
| 4,981,698 A | 1/1991 | Cherukuri et al. |
| 4,985,236 A | 1/1991 | Ibrahim et al. |
| 4,986,991 A | 1/1991 | Yatka et al. |
| 4,997,659 A | 3/1991 | Yatka et al. |
| 5,004,595 A | 4/1991 | Cherukuri et al. |
| 5,009,900 A | 4/1991 | Levine et al. |
| 5,017,385 A | 5/1991 | Wienecke |
| 5,043,154 A | 8/1991 | Gaffar et al. |
| 5,043,169 A | 8/1991 | Cherukuri et al. |
| 5,057,327 A | 10/1991 | Yatka et al. |
| 5,057,328 A | 10/1991 | Cherukuri et al. |
| 5,059,429 A | 10/1991 | Cherukuri et al. |
| 5,064,658 A | 11/1991 | Cherukuri et al. |
| 5,073,389 A | 12/1991 | Wienecke |
| 5,080,877 A | 1/1992 | Chane-Ching et al. |
| 5,082,671 A | 1/1992 | Cherukuri |
| 5,084,278 A | 1/1992 | Mehta |
| 5,096,699 A | 3/1992 | Gaffar et al. |
| 5,096,701 A | 3/1992 | White, Jr. et al. |
| 5,100,678 A | 3/1992 | Reed et al. |
| 5,108,763 A | 4/1992 | Chau et al. |
| 5,126,151 A | 6/1992 | Bodor et al. |
| 5,139,793 A | 8/1992 | Johnson et al. |
| 5,139,794 A | 8/1992 | Patel et al. |
| 5,139,798 A | 8/1992 | Yatka et al. |
| 5,154,939 A | 10/1992 | Broderick et al. |
| 5,164,210 A | 11/1992 | Campbell et al. |
| 5,169,657 A | 12/1992 | Yatka et al. |
| 5,169,658 A | 12/1992 | Yatka et al. |
| 5,174,514 A | 12/1992 | Prodi |
| 5,176,900 A | 1/1993 | White, Jr. et al. |
| 5,198,251 A | 3/1993 | Song et al. |
| 5,202,112 A | 4/1993 | Prencipe et al. |
| 5,208,009 A | 5/1993 | Gaffar et al. |
| 5,226,335 A | 7/1993 | Sitte et al. |
| 5,227,182 A | 7/1993 | Song et al. |
| 5,229,148 A | 7/1993 | Copper |
| 5,240,710 A | 8/1993 | Bar-Shalom et al. |
| 5,256,402 A | 10/1993 | Prencipe et al. |
| 5,273,741 A | 12/1993 | Gaftar et al. |
| 5,300,283 A | 4/1994 | Prencipe et al. |
| 5,334,375 A | 8/1994 | Nabi et al. |
| 5,334,396 A | 8/1994 | Yatka |
| 5,336,509 A | 8/1994 | McGrew et al. |
| 5,352,439 A | 10/1994 | Norfleet et al. |
| 5,364,627 A | 11/1994 | Song |
| 5,380,530 A | 1/1995 | Hill |
| 5,385,729 A | 1/1995 | Prencipe et al. |
| 5,391,315 A | 2/1995 | Ashkin |
| 5,413,799 A | 5/1995 | Song et al. |
| 5,415,880 A | 5/1995 | Song et al. |
| 5,431,930 A | 7/1995 | Patel et al. |
| 5,437,876 A | 8/1995 | Synosky et al. |
| 5,437,878 A | 8/1995 | Panhorst et al. |
| 5,462,754 A | 10/1995 | Synosky et al. |
| 5,474,787 A | 12/1995 | Grey et al. |
| 5,480,668 A | 1/1996 | Nofre et al. |
| 5,487,902 A | 1/1996 | Andersen et al. |
| 5,498,378 A | 3/1996 | Tsaur et al. |
| 5,501,864 A | 3/1996 | Song et al. |
| 5,503,823 A | 4/1996 | Norfleet et al. |
| 5,505,933 A | 4/1996 | Norfleet et al. |
| 5,523,098 A | 6/1996 | Synosky et al. |
| 5,532,004 A | 7/1996 | Bell et al. |
| 5,582,816 A | 12/1996 | Mandanas et al. |
| 5,589,160 A | 12/1996 | Rice |
| 5,589,194 A | 12/1996 | Tsuei et al. |
| 5,599,527 A | 2/1997 | Hsu et al. |
| 5,603,920 A | 2/1997 | Rice |
| 5,603,971 A | 2/1997 | Porzio et al. |
| 5,618,517 A | 4/1997 | Miskewitz |
| 5,626,892 A | 5/1997 | Kehoe et al. |
| 5,629,035 A | 5/1997 | Miskewitz |
| 5,637,618 A | 6/1997 | Kurtz et al. |
| 5,645,821 A | 7/1997 | Libin |
| 5,651,958 A | 7/1997 | Rice |
| 5,658,553 A | 8/1997 | Rice |
| 5,676,932 A | 10/1997 | Wason et al. |
| 5,693,334 A | 12/1997 | Miskewitz |
| 5,698,215 A | 12/1997 | Kalili et al. |
| 5,702,687 A | 12/1997 | Miskewitz |
| 5,713,738 A | 2/1998 | Yarborough |
| 5,716,601 A | 2/1998 | Rice |
| 5,736,175 A | 4/1998 | Cea et al. |
| 5,756,074 A | 5/1998 | Ascione et al. |
| 5,789,002 A | 8/1998 | Duggan et al. |
| 5,800,848 A | 9/1998 | Yatka et al. |
| 5,824,291 A | 10/1998 | Howard |
| 5,869,028 A | 2/1999 | McGill et al. |
| 5,879,728 A | 3/1999 | Graff et al. |
| 5,912,007 A | 6/1999 | Pan et al. |
| 5,939,051 A | 8/1999 | Santalucia et al. |
| 6,027,746 A | 2/2000 | Lech |
| 6,056,992 A | 5/2000 | Lew |
| 6,174,514 B1 | 1/2001 | Cherukuri et al. |
| 6,190,644 B1 | 2/2001 | McClanahan et al. |
| 6,239,690 B1 | 5/2001 | Burbidge et al. |
| 6,261,540 B1 | 7/2001 | Nelson |
| 6,290,933 B1 | 9/2001 | Durga et al. |
| 6,365,209 B2 | 4/2002 | Cherukuri |
| 6,379,654 B1 | 4/2002 | Gebreselassie et al. |
| 6,416,744 B1 | 7/2002 | Robinson et al. |
| 6,428,827 B1 | 8/2002 | Song et al. |
| 6,471,945 B2 | 10/2002 | Luo et al. |
| 6,475,469 B1 | 11/2002 | Montgomery |
| 6,479,071 B2 | 11/2002 | Holme et al. |
| 6,485,739 B2 | 11/2002 | Luo et al. |
| 6,506,366 B1 | 1/2003 | Leinen et al. |
| 6,534,091 B1 | 3/2003 | Garces Garces et al. |
| 6,555,145 B1 | 4/2003 | Cherukuri |
| 6,685,916 B1 | 2/2004 | Holme et al. |
| 6,692,778 B2 | 2/2004 | Yatka et al. |
| 6,696,044 B2 | 2/2004 | Luo et al. |
| 6,759,066 B2 | 7/2004 | Savage et al. |
| 7,022,352 B2 | 4/2006 | Castro et al. |
| 7,025,999 B2 | 4/2006 | Johnson et al. |
| 2002/0044968 A1 | 4/2002 | Van Lengerich |
| 2002/0054859 A1 | 5/2002 | Alvarez Hernandez |
| 2002/0122842 A1 | 9/2002 | Seielstad et al. |
| 2002/0150616 A1 | 10/2002 | Vandecruys |
| 2003/0059519 A1 | 3/2003 | Merkel et al. |
| 2003/0077362 A1 | 4/2003 | Panhorst et al. |
| 2003/0091721 A1 | 5/2003 | Ohta et al. |
| 2003/0099740 A1 | 5/2003 | Colle et al. |
| 2003/0113274 A1 | 6/2003 | Holme et al. |
| 2004/0136928 A1 | 7/2004 | Holme et al. |
| 2004/0146599 A1 | 7/2004 | Andersen et al. |
| 2004/0175489 A1 | 9/2004 | Clark et al. |
| 2004/0238993 A1 | 12/2004 | Benczedi et al. |
| 2005/0025721 A1 | 2/2005 | Holme et al. |
| 2005/0112236 A1 | 5/2005 | Boghani et al. |
| 2005/0214348 A1 | 9/2005 | Boghani et al. |
| 2005/0220867 A1 | 10/2005 | Boghani et al. |
| 2005/0260266 A1 | 11/2005 | Gebreselassie et al. |
| 2006/0034897 A1 | 2/2006 | Boghani et al. |
| 2006/0068057 A1 | 3/2006 | Boghani et al. |
| 2006/0068059 A1 | 3/2006 | Boghani et al. |
| 2006/0193896 A1 | 8/2006 | Boghani et al. |
| 2006/0263413 A1 | 11/2006 | Boghani et al. |
| 2006/0263472 A1 | 11/2006 | Boghani et al. |
| 2006/0263473 A1 | 11/2006 | Boghani et al. |
| 2006/0263477 A1 | 11/2006 | Boghani et al. |
| 2006/0263478 A1 | 11/2006 | Boghani et al. |
| 2006/0263479 A1 | 11/2006 | Boghani et al. |
| 2006/0263480 A1 | 11/2006 | Boghani et al. |
| 2007/0298061 A1 | 12/2007 | Boghani et al. |

(56) References Cited

U.S. PATENT DOCUMENTS

| | | |
|---|---|---|
| 2008/0063747 A1 | 3/2008 | Boghani et al. |
| 2008/0160138 A1 | 7/2008 | Boghani et al. |
| 2008/0166449 A1 | 7/2008 | Kabse et al. |
| 2008/0187621 A1 | 8/2008 | Boghani et al. |
| 2008/0199564 A1 | 8/2008 | Boghani et al. |
| 2009/0098252 A1 | 4/2009 | Boghani et al. |
| 2009/0175982 A1 | 7/2009 | Boghani et al. |
| 2009/0220642 A1 | 9/2009 | Boghani et al. |

FOREIGN PATENT DOCUMENTS

| | | | |
|---|---|---|---|
| DE | 196 53 100 | 7/1998 | |
| EP | 0 067 595 | 12/1982 | |
| EP | 0 134 120 | 8/1984 | |
| EP | 0 252 374 | 1/1988 | |
| EP | 0 608 712 | 8/1994 | |
| EP | 0 132 444 | 2/1995 | |
| GB | 875763 | 8/1961 | |
| GB | 1444024 | 7/1976 | |
| GB | 2 388 581 | 11/2003 | |
| JP | 62-215349 | 9/1987 | |
| JP | 02-227044 | 9/1990 | |
| JP | 5-38258 | 2/1993 | |
| JP | 5-292890 | 11/1993 | |
| JP | 2623769 | 6/1997 | |
| JP | 2008-539801 | 11/2008 | |
| JP | 2008-540690 | 11/2008 | |
| WO | WO 85/03414 | 8/1985 | |
| WO | WO 88/00463 | 1/1988 | |
| WO | WO 89/11212 | 11/1989 | |
| WO | WO 90/04926 | 5/1990 | |
| WO | WO 90/07859 | 7/1990 | |
| WO | WO 90/12512 | 11/1990 | |
| WO | WO 90/13994 | 11/1990 | |
| WO | WO 91/07104 | 5/1991 | |
| WO | WO 92/02145 | 2/1992 | |
| WO | WO 92/06160 | 4/1992 | |
| WO | WO 95/33034 | 12/1995 | |
| WO | WO 96/08166 | 3/1996 | |
| WO | WO 96/19193 | 6/1996 | |
| WO | WO 96/20608 | * 7/1996 | ............... A23G 3/30 |
| WO | WO 97/02009 | 1/1997 | |
| WO | WO 97/02011 | 1/1997 | |
| WO | WO 98/18339 | 5/1998 | |
| WO | WO 98/23165 | 6/1998 | |
| WO | WO 98/29088 | 7/1998 | |
| WO | WO 99/15032 | 4/1999 | |
| WO | WO 99/15192 | 4/1999 | |
| WO | WO 99/27798 | 6/1999 | |
| WO | WO 99/43294 | 9/1999 | |
| WO | WO 00/01253 | 1/2000 | |
| WO | WO 00/35296 | 6/2000 | |
| WO | WO 00/35398 | 6/2000 | |
| WO | WO 00/69282 | 11/2000 | |
| WO | WO 00/75274 | 12/2000 | |
| WO | WO 02/055649 | 7/2002 | |
| WO | WO 02/076231 | 10/2002 | |
| WO | WO 02/000039 | 11/2002 | |
| WO | WO 02/102362 | 12/2002 | |
| WO | WO 03/063604 | 8/2003 | |
| WO | WO 2004/006967 | 1/2004 | |
| WO | WO 2004/077956 | 9/2004 | |
| WO | WO 2005/016022 | 2/2005 | |
| WO | WO 2005/051427 A1 | 6/2005 | |
| WO | WO 2005/079598 | 9/2005 | |
| WO | WO 2005/087020 | 9/2005 | |
| WO | WO 2005/091918 | 10/2005 | |
| WO | WO 2006/003349 | 1/2006 | |
| WO | WO 2006/079056 | 7/2006 | |
| WO | WO 2006/086061 | 8/2006 | |

OTHER PUBLICATIONS

Anonymous; "HLB Systems" [Online] pp. 1-4, XP002401202. Retrieved from the Internet: URL:http://pharmal.tripod.com/ch17.htm. (retrieved Sep. 28, 2006).
Ovejero-Lopez et al.; Flavor Release Measurement from Gum Model System; J.Agric. Food Chem.; 2004, vol. 52, pp. 8119-8126.
Rassing, M.R.; Chewing Gum as a Drug Delivery System; Advanced Drug Delivery Reviews, 1994; vol. 13, No. 1-2; pp. 89-121.
JP 02083030 A—Lion Corp., "Microcapsule for Foods", Mar. 23, 1990, Abstract.
Prencipe et al.; Squeezing out a better toothpaste; Chemtech, Dec. 1995;http://pubs.acs.org/hotartcl/chemtech/95/dec/dec.html; printed Apr. 20, 2004; pp. 1-7.
Gantrez® AN; ISP Polymers for Oral Care; http://www.ispcorp.com/products/oralcare/content/brochure/oral/prod.html, printed Jun. 9, 2004, pp. 1-5.
Demmers et al.; Effect of Surfactants and Proteolytic Enzymes on Artificial Calculus Formation; Surfactants and Enzymes: Calculus; pp. 28-35.

* cited by examiner

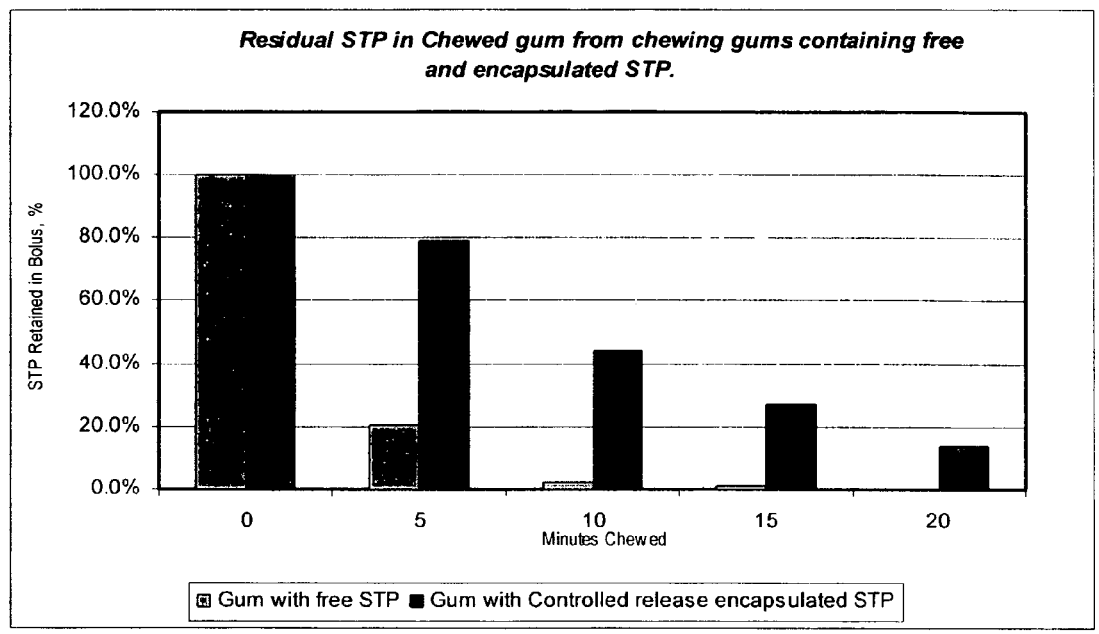

CONTROLLED RELEASE ORAL DELIVERY SYSTEMS

CROSS REFERENCE TO RELATED APPLICATIONS

The present application is a continuation-in-part of PCT US04/37185, filed Nov. 22, 2004, and a continuation-in-part of U.S. application Ser. No. 11/083,968, filed Mar. 21, 2005 now U.S. Pat. No. 8,828,423 (the U.S. National Phase filing of PCT US04/37185), which are both continuations-in-part of U.S. application Ser. No. 10/719,298, filed Nov. 21, 2003 now abandoned, the contents all of which are incorporated herein by reference in their entirety.

FIELD

The present invention is generally directed to oral delivery systems including an encapsulated active ingredient. In particular, the invention relates to an oral delivery system in which at least one active component is encapsulated in a polymer matrix. In some embodiments, the polymer matrix may have a tensile strength within a desirable range and/or may include at least one hydrophobic polymer to provide controlled release of the active.

BACKGROUND

Unblemished white teeth have long been considered cosmetically desirable. Unfortunately, in the absence of thorough dental cleaning, teeth can become discolored or stained from color-causing substances present in food, beverages, tobacco, and the like, and internal sources such as blood, amalgam-based fillings, and antibiotics (e.g., tetracycline).

Currently, there are a number of methods for removing stains in teeth. These methods are generally based on the use of abrasives, hydrolytic agents or oxidizing agents to break down the staining material. For example, mechanical methods of tooth cleaning are known whereby the stain is mechanically abraded through the use of abrasives or polishing agents normally employed in toothpaste preparations. Typical preparations containing abrasives are toothpastes, gels or powder dentifrices, which require close contact with the teeth. Typical abrasives include hydrated silica, calcium carbonate, sodium bicarbonate and alumina.

Hydrolytic agents, such as proteolytic enzymes, can also be used to whiten teeth. These products are usually in the form of pastes or gels, and function to whiten teeth by removing the plaque and calculus that have entrapped the stain.

Oxidizing agents such as urea peroxide, hydrogen peroxide or calcium peroxide, represent the most common forms of whitening agents for tooth enamels. It is believed that peroxides whiten teeth by releasing hydroxyl radicals capable of breaking down the plaque/stain complex into a form that can be flushed away or removed by an abrasive.

Other active stain-removing components include surface-active agents, such as anionic surfactants and chelators, which have been incorporated into stain-removing compositions because of their stain-removing properties. For example, anionic surfactants typically employed in dentifrice compositions include sodium lauryl sulfate and sodium N-lauryl sarcosinate. Furthermore, chelators, such as polyphosphates, are typically employed in dentifrice compositions as tartar control ingredients. For example, tetrasodium pyrophosphate and sodium tri-polyphosphate are typical ingredients found in such compositions.

Stain-removing gum compositions are known. For example, gum compositions including sodium tripolyphosphate and xylitol are known. Also, gum compositions are known, which include hexametaphosphate and an abrasive silica material. Moreover, a dental gum is known, which includes sodium tripolyphosphate, tetrasodium pyrophosphate, a silica abrasive and zinc acetate. A whitening gum composition is also known, which includes the abrasives sodium bicarbonate and calcium carbonate, and is sold under the brand name V6®.

Moreover, stain-removing gum compositions are known that include anionic surfactants such as fatty acid salts. For example, sodium stearate is a fatty acid salt employed in a gum product sold under the brand name Trident White® (see U.S. Pat. Nos. 6,471,945, 6,479,071 and 6,696,044). Furthermore, copending, commonly-owned U.S. patent application Ser. No. 10/901,511 discloses stain-removing gum compositions containing a salt of ricinoleic acid.

Current delivery systems for oral care/tooth whitening actives present problems. For example, the release of actives from tablets, films, mouthwashes, toothpastes and gels is quite rapid and occurs for a short period of time. Most of these products produce temporary, elevated levels of actives, followed by a rapid decrease to zero levels. Similarly, some tooth whitening actives can be released at elevated levels from gum bases within a few minutes following mastication, followed by a rapid decrease to low levels.

Encapsulating materials have been used previously to encapsulate sweeteners, acids, flavorings, soluble dietary fibers, biologically active agents, breath freshening agents, and the like. Such encapsulating materials have included, for example, cellulose and its derivatives, arabinogalactin, gum arabic, polyolefins, waxes, vinyl polymers, gelatin and zein. In general, encapsulating actives in edible compositions has been used to slow their degradation, to enhance the uniformity of their release, and to prolong their release in a controlled manner.

The selection of a suitable encapsulating material (e.g., polyvinyl acetate, PVAc) has usually been focused on the molecular weight of the encapsulating material, with higher molecular weights generally associated with longer release times. However, this approach is limited in that a predictable modification of the release profile of an active is made only through the modification of the molecular weight of the encapsulating material.

In view of the foregoing, it would be beneficial to provide oral delivery systems wherein a controlled amount of an oral care active is delivered to an oral cavity over a longer period of time, rather than delivering a high concentration of the active followed by no active. In particular, it would be advantageous to encapsulate at least one oral care active in a suitable polymer matrix to enhance the uniformity of its release, and to prolong its release in a controlled manner. In some embodiments, the release profile of the active may be modified by selection of a polymer matrix having a tensile strength within a desirable range and/or may be modified by including in the matrix a polymer having a water absorption within a desirable range.

SUMMARY OF THE INVENTION

The present invention is generally directed to oral delivery systems in which an active component has been effectively encapsulated in a polymer matrix. The oral delivery systems are for use in edible compositions. The polymer matrix prolongs the release of the active in a controlled manner and/or enhances the uniformity of the release of the active. In so doing, the active remains available for its intended purpose in the oral cavity for a longer period of time as compared to an edible composition wherein the active component is free. This will be discussed in greater detail below.

In one aspect of the present invention, there is provided an oral delivery system including at least one active component; and a polymer matrix at least partially encapsulating the at least one active component. The polymer matrix may have a tensile strength of at least about 6,500 psi and/or may include at least one polymer having a water absorption of about 0.01% to about 50% by weight.

The oral compositions of this invention may include, but are not limited to, any number of compositions, including gums, confectionary compositions, toothpastes and mouthwashes. For example, certain aspects of the present invention relate to tooth whitening gum compositions.

In some embodiments, the gum composition includes a gum base; and a delivery system. The delivery system for use in the gum composition includes at least one active component; and a polymer matrix at least partially encapsulating the at least one active component. The polymer matrix may have a tensile strength of at least about 6,500 psi and/or may include at least one polymer having a water absorption of about 0.01% to about 50% by weight.

Other aspects of the present invention relate to methods of preparing and using the inventive oral delivery compositions provided herein.

In some embodiments, a method of preparing an oral delivery system includes at least partially encapsulating the least one active component in a polymer matrix, thereby forming an oral delivery system. The polymer matrix may have a tensile strength of at least about 6,500 psi and/or may include at least one polymer having a water absorption of about 0.0.1% to about 50% by weight.

The oral delivery systems of the present invention may be prepared in any number of ways. For example, the active component(s) can be at least partially encapsulated by the polymer using extrusion. The active component(s) can also be at least partially encapsulated using a high shear mixer, such as a sigma or Banbury mixer to mix the active component(s) with a polymer melt. In another example, the active component(s) can be at least partially encapsulated by using a spray coating of fluidized particles of the polymer.

The present invention also provides a method of preparing an oral composition, such as an oral care composition. The method includes providing an oral delivery system; and combining the oral delivery system with a carrier composition. The oral delivery system for use in preparing the oral composition includes at least one active component; and a polymer matrix at least partially encapsulating the at least one active component. The polymer matrix may have a tensile strength of at least about 6,500 psi and/or may include at least one polymer having a water absorption of about 0.01% to about 50% by weight.

One particular aspect of the present invention relates to a method of preparing a gum composition. In some embodiments, this method includes at least partially encapsulating at least one active component in a polymer matrix. The polymer matrix may have a tensile strength of at least about 6,500 psi and/or may include at least one polymer having a water absorption of about 0.01% to about 50%. The method further includes heating a gum base to soften the base; and mixing the softened gum base with the at least partially encapsulated active component to obtain a substantially homogeneous mixture. The method also includes cooling the mixture; and forming the cooled mixture into gum pieces.

Further provided is a method of controlling the release of an active component from an oral delivery system. This method includes providing the oral delivery system of the present invention; and employing the oral delivery system in an oral cavity, whereby a controlled amount of the at least one active component is released into the oral cavity.

BRIEF DESCRIPTION OF THE DRAWING

The FIGURE is a graphical representation of the percentage of sodium tripolyphosphate (STP) that is retained in the bolus of a chewing gum versus the minutes chewed for chewing gum compositions including free (control), and encapsulated STP (inventive).

DETAILED WRITTEN DESCRIPTION

The present invention provides a delivery system for active components. The delivery system is for use in edible compositions, such as gum compositions. The delivery system includes an encapsulating material and at least one active component. The encapsulating material at least partially forms a physical barrier around the at least one active. This physical barrier prolongs the release of the active in an oral cavity in a controlled manner and/or enhances the uniformity of the release of the active in an oral cavity. In so doing, the active remains available for its intended purpose in the oral cavity for a longer period of time as compared to an edible composition wherein the active component is free.

As used herein the transitional term "comprising," (also "comprises," etc.) which is synonymous with "including," "containing," or "characterized by," is inclusive or open-ended and does not exclude additional, unrecited elements or method steps, regardless of its use in the preamble or the body of a claim.

As used herein, the term "gum compositions" is intended to include any gum compositions, including "chewing gum" and "bubble gum."

As used herein, the term "active component" refers to any encapsulated material included in the compositions of the present invention, wherein the active provides some desirable property upon release from encapsulation (for example, when the encapsulated material has been subjected to mastication). Examples of suitable actives include oral care actives, such as surfactants, anticalculus agents, hydrolytic agents (e.g., enzymes), bleaching or whitening agents, antibacterial agents, anticaries agents, dental remineralization agents, desensitizing agents, agents to counter breath odor or breath freshening agents, plaque acid buffering agents and sweeteners (e.g., high intensity sweeteners). Other examples of suitable actives include flavors, medicaments, vitamins, taste masking agents, etc.

The term "oral delivery system" as used herein is meant to encompass the polymer matrix and at least one active component, which is at least partially encapsulated by the polymer matrix. The term is also meant to include other additives, which may be used to form the oral delivery system (e.g., a solvent, a plasticizer, a filler, etc.). It will be understood that oral compositions (e.g., edible compositions) of the present invention may include a plurality of delivery systems, if desired.

By the term "at least partially encapsulating", it is meant that the polymer matrix at least partially forms a physical barrier around the at least one active component. Such a barrier may be formed, for example, when a polymer melt and at least one active are mixed under high shear conditions using an extruder, or other high shear mixer. The barrier may also be formed as a polymer coating (e.g., spray coating), or a polymer film, which at least partially surrounds the at least one active, for example.

The oral delivery systems of the present invention are for use in edible compositions. The compositions of the present invention may be in a form selected from, for example, dentifrices including mouthwashes, mouthrinses, toothpastes, tooth powders, tooth hardeners, antiplaque compositions, dental creams, dental flosses, liquids, gels, and the like; chewing gums, including center-filled gums, and the like; and confectionaries, including mints, lozenges, and the like. In some embodiments, the compositions of the present invention are in the form of chewing gums.

In some embodiments, the present invention is directed to compositions with stain-removing properties for producing a whitening effect on dental surfaces that are treated with the same. Such compositions are especially suitable for removing stains, which adhere to, or are entrapped in materials on, the surface of teeth and for preventing build-up of the stain entrapping material and stains on dental surfaces. The compositions of the present invention are retained in the oral cavity for a sufficient time to contact the dental surfaces for purposes of providing beneficial dental effects.

An ingredient in an edible composition will have a release profile when a consumer consumes the edible composition. In some embodiments, the ingredient may be released by mechanical action of the chewing, and/or by chemical action or reaction of the ingredient with another ingredient or saliva or other material in the consumer's mouth. The release profile for the ingredient is indicative of the availability of the ingredient in the consumer's mouth to interact with receptors (e.g., taste receptors), mucous membranes, teeth, etc. in the consumer's mouth. An edible composition may include the same or different release profiles for different ingredients. In some embodiments, the release profile for only a finite number (e.g., one or two) of ingredients may be of primary importance.

The release profile of an ingredient in an edible composition can be influenced by many factors such as, for example, rate of chewing, intensity of chewing, the amount of the ingredient, form of the ingredient added to the edible composition (e.g., encapsulated in a delivery system, unencapsulated, pretreated), how the edible composition is mixed or otherwise prepared, when or how the ingredient is added to other ingredients in the edible composition, the ratio of the amount of the ingredient to the amount of one or more other ingredients in the edible composition, the ratio of the amount of the ingredient to the amount of one or more other ingredients in a delivery system that is included in the edible composition, etc.

In some embodiments, a release profile for an ingredient may be related to a specific time period. For example, release of an ingredient from a delivery system may increase during a first time period, reach a peak, and then decrease during a second time period. Thus, in some embodiments, a release profile for an ingredient may include one or more time periods, each of which has an associated release rate (which may or may not be known or measurable). The time periods may be the same length of time or may be different lengths of time. A first time period may have a fixed or varied release rate for the ingredient during the first time period and an average release rate for the ingredient over the first time period. Similarly, a second time period may have a fixed or varied release rate for the ingredient during the second time period and an average release rate for the ingredient over the second time period. In some embodiments, a release profile for an ingredient in an edible composition may include only one time period or be related to only a single point in time, both of which typically relate or are relative to when consumption of the edible composition has started. In other embodiments, a release profile may relate to two or more time periods and/or two or more points in time, all of which typically relate or are relative to when consumption of the edible product has started.

In some embodiments, a release profile may be defined or characterized by one or more factors or characteristics, even if other or all aspects of the release profile are not determined, selected, or even known. Thus, in some embodiments, a release profile for an ingredient may include only one characteristic. For example, characteristics may include one or more of the following: release rate of an ingredient during a time period, a specific time period during which a minimum, average, or predominant amount of an ingredient is released during consumption of an edible composition that includes the ingredient (even if some of the ingredient is released before or after the specific time period and even if the release rate during the time period is not specified or varies), a specific time after which a minimum, average, or predominant amount of an ingredient is released during consumption of an edible composition that includes the ingredient (even if some of the ingredient is released before the specific time and even if the release rates are or are not specified), etc.

In some embodiments, managing a release profile for one or more ingredients may include changing or otherwise managing the starting and ending times for the time periods, changing or otherwise managing the lengths of the time periods, and/or changing or otherwise managing the release rates during the time periods. For example, managing a release profile may include changing or managing a release rate during a time period. An ingredient can be released more quickly or earlier during a first or second time period by increasing its release rate during these time periods. Likewise, the ingredient can be released more slowly or in a more delayed manner during the first or second time periods by decreasing its release rate during these time periods. As another example, managing a release profile may include shifting the start and end of the time periods in the release profile, but the length of the time periods may stay the same and the release rates of the ingredient(s) during the time periods may stay the same (e.g., the release of an ingredient may be managed to delay the release of the predominant amount of the ingredient by one minute, five minutes, ten minutes, thirty minutes, etc.). As a third example, managing a release profile may include shifting the start or end of one or more time periods and changing the release rate within the one or more time periods.

In some embodiments, causing a delay in a release of an ingredient in an edible composition includes causing a delay in the release or availability of the predominant amount of the ingredient after consumption of the edible product begins and/or causing release or availability of a desire, predominant, or minimum amount of the ingredient at a certain time, after a certain time, or during a desired time period after consumption of the edible composition begins. In some embodiments, none of the ingredient will be released or become available before the certain time or before or after the desired time period. In other embodiments, some of the ingredient may be released or become available before the certain time and/or before or after the desired time period.

In some embodiments, determining or selecting a desired release profile may include determining or selecting one or more factors or characteristics of the desired release profile, as previously described above. The factors or characteristics than serve to define or characterize the release profile, even if other or all aspects of the release profile are not determined or selected. Thus, determining or selecting a release profile for an ingredient can includes situations where only one characteristic for the release of the ingredient is determined or selected. In some embodiments, a characteristic may be determined or measured by one or more techniques or methods such as, for example, chemical and/or mechanical testing and analysis, consumer testing, descriptive or expert taste or chew panel, other in vivo or in vitro testing, etc.

In accordance with the present invention, an oral care active may be employed in the compositions of the present invention. Such an active may be, but is not limited to, a tooth whitening active. For example, the encapsulated tooth whitening active may be one or more of the following: anticalculus agents, such as polyphosphate salts, surfactants, such as fatty acid salts, hydrolytic agents, such as proteolytic enzymes, and oxidizing agents, such as peroxides. Such agents facilitate the effective removal of dental stains. Other oral care actives include, for example, desensitizing agents, dental remineralization agents, antibacterial agents, anticaries agents, agents to counter breath odor or breath freshening agents and plaque acid buffering agents.

As described above, the release of non-encapsulated oral care actives from tablets, films, mouthwashes, toothpastes and gels is quite rapid and occurs for a short period of time. Most of these products produce temporary, elevated levels of actives, followed by a rapid decrease to zero levels. Similarly, some tooth whitening actives can be released at elevated levels from gum bases within a few minutes following mastication, followed by a rapid decrease to low levels. The present invention is directed to overcoming this problem by encapsulating the active(s) in a suitable polymer matrix.

For example, by encapsulating the active within a suitable polymer matrix, the present inventors have found that they can enhance the uniformity of an active's release, and prolong the active's release in a controlled manner. In some embodiments, the release profile of the active may be modified by selection of a polymer matrix having a tensile strength within a desirable range and/or may be modified by including in the matrix a polymer having a water absorption within a desirable range.

In some embodiments, a polymer matrix useful in the present invention has a tensile strength of at least about 6,500 psi. In some embodiments, the polymer matrix has a tensile strength of about 20,000 to about 50,000 psi. The tensile strength may be measured by ASTM D638.

In some embodiments, the polymer matrix includes at least one polymer having a water absorption of about 0.01% to about 50% by weight. In some embodiments, the water absorption of the at least one polymer is measurable by ASTM D570-98. In some embodiments, the at least one polymer has a water absorption of about 0.1% to about 15% by weight.

The at least one polymer of the polymer matrix provides a physical barrier around the at least one active component. In some embodiments, the polymer may be selected from at least one of the following: polyvinyl acetate, polyvinylacetate phthalate, polymethylmethacrylate, polyethylene terephthalate and combinations thereof. The polymer matrix may further include a solvent, a plasticizer, a filler or a combination of these.

In some embodiments, the delivery system, when used in an oral composition, releases a controlled amount of the active component in an oral cavity over a longer period of time as compared to an oral composition wherein the active component is free. In one embodiment, this period of time is about 5 to about 60 minutes.

The present inventors have found that, when employed in a chewing gum composition, an oral delivery system of the present invention was useful for controlling and sustaining the release of actives in the oral cavity.

In some embodiments, at least about 50% of the active component remains in the oral composition after the time period of about 5 to about 60 minutes. For example, as shown in the Examples below, in vitro chew-out studies showed that chewing gum containing an inventive oral delivery system delayed the release of tooth whitening actives significantly during at least 30 minutes of chewing time as compared to a chewing gum containing free actives. This is significant because tooth whitening actives, if not released quickly, are not efficacious.

As described above, the oral delivery systems of the present invention include at least one active component. In some embodiments the at least one active component is selected from the following: anticalculus agents, abrasive agents, oral cleaning agents, bleaching or whitening agents, densensitizing agents, dental remineralization agents, surfactants, antibacterial agents, anticaries agents, agents to counter breath odor or breath freshening agents, plaque acid buffering agents, sweetening agents, cooling agents, warming agents, herbal agents, medicaments, vitamins, taste masking agents and combinations thereof.

In one desired embodiment, the at least one active component is an anticalculus agent and a taste masking agent. Examples of anticalculus agents include polyphosphates and sodium bicarbonate. Such anticalculus agents may be bitter in taste. Therefore, in some desired embodiments, the anticalculus agent (or any other unpleasant tasting active) may be encapsulated along with at least one taste masking agent. In some embodiments, the taste masking agent is a sweetener, such as an intense sweetener.

As described above, a suitable active for encapsulation may be a tooth whitening active. A tooth whitening active is preferably employed in the compositions of the present invention in a stain-removing effective amount. The stain-removing effective amount is an amount of the tooth whitening active that is sufficient to prevent, eliminate, or at least reduce, the presence of stains on dental surfaces in warm-blooded animals including humans, but low enough to avoid any undesirable side effects. This stain-removing effective amount of a tooth whitening active(s) may vary with the type and extent of the particular stain, the age and physical condition of the warm-blooded animal, including humans being treated, the duration of treatment, the nature of concurrent therapy, the specific tooth whitening active employed, and the particular carrier from which the tooth whitening active is applied.

The concentration of a tooth whitening active(s) in a composition of the present invention depends on the type of composition (e.g., toothpaste, mouthwash and rinse, lozenge, chewing gum, confectionary, and the like) used to apply the tooth whitening active(s) to the dental surfaces, due to the differences in the efficiency of the compositions contacting the teeth and due also to the effective amount of the composition generally used. The concentration may also depend on the levels of the stains present.

Except as otherwise noted, the amount of the components incorporated into the compositions according to the present invention is designated as percentage by weight based on the total weight of the composition.

As described above, an oral composition of the present invention can be a gum composition, such as chewing gum composition. The chewing gum compositions of the present invention may be coated or uncoated, and be in the form of slabs, sticks, pellets, balls and the like. The composition of the different forms of the chewing gum compositions will be similar but may vary with regard to the ratio of the components. For example, coated gum compositions may contain a lower percentage of softeners. Pellets and balls may have a chewing gum core, which has been coated with either a sugar solution or a sugarless solution to create the hard shell. Slabs and sticks are usually formulated to be softer in texture than the chewing gum core.

Center-filled gum is another common gum form. The gum portion has a similar composition and mode of manufacture to that described above. However, the center-fill is typically an aqueous liquid or gel, which is injected into the center of the gum during processing. A suitable encapsulated active(s) could optionally be incorporated into the center-fill during manufacture of the fill, incorporated directly into the chewing gum portion of the total gum composition, or both. The center-filled gum may also be optionally coated and may be prepared in various forms, such as in the form of a lollipop.

In some embodiments of the present invention, a coated gum may be formed, wherein the encapsulated active(s) is in at least one of the core or the gum coating. For example, an encapsulated abrasive agent may be incorporated into the coating, and encapsulated surface actives (e.g., surfactant and/or anticalculus agent) may be incorporated into the gum base. By providing an encapsulated abrasive in the coating, the stain is first mechanically abraded by the abrasive in combination with chewing, which requires close contact with the teeth. Whereas the abrasive continues to have a chemical effect in removing the stain after it is released from the coating into the saliva, it may be advantageous to enhance the mechanical abrasion initially by providing it in the coating layer. Furthermore, the coating provides another effective vehicle for delivering an encapsulated surface-active.

It is also well within the contemplation of the present invention that encapsulated active(s) can be incorporated into the gum base. The gum base provides another effective vehicle for delivering the active(s), such as abrasives and surface-active agents because it permits protracted contact of the active(s) with the teeth. For example, a tooth whitening agent(s) can chemically remove the stain once released from the gum base and/or gum coating into saliva. The oral delivery systems of the present invention, when employed in tooth whitening gums or other oral care compositions, permit controlled and sustained release of the active(s) in the oral cavity. This improves the efficacy of the active.

Chewing gum compositions of the present invention may include a gum base and most of the other typical chewing composition components, such as sweeteners, softeners, flavorants and the like. At least one encapsulated oral care active, such as a tooth whitening active, is employed in some embodiments of the gum compositions.

Surfactants

The oral compositions of the present invention may include encapsulated tooth whitening agent(s) as provided herein. For example, in some embodiments the at least one active component employed in the oral delivery system is a surfactant. Suitable surfactants may include anionic surfactants and non-ionic surfactants or mixtures thereof. Anionic surfactants useful herein include medium and long chain fatty acid esters and salts. In some embodiments, the anionic surfactant is a water-soluble salt of a fatty acid having from 14 to 25 carbon atoms. The salt may include a metal ion that can be a divalent metal ion or a monovalent metal ion. For example, the metal ion can be selected from sodium, potassium, calcium, magnesium and combinations thereof.

Suitable examples of fatty acid salts include salts of stearate and palmitrate. Other examples include hydroxy fatty acid salts, such as salts of ricinoleic acid, castor oil and ergot oil. In some embodiments, the fatty acid salt is sodium stearate or sodium ricinoleate.

Ricinoleic acid accounts for about 90% of the triglyceride fatty acids of castor oil, and up to about 40% of the glyceride fatty acids of ergot oil. Other suitable hydroxy fatty acid salts include, but are not limited to, those derived from the following: lesquerolic acid, densipolic acid, auricolic acid and β-dimorphecolic acid. Combinations of hydroxy fatty acid salts may also be employed.

The water-soluble salts of hydroxy fatty acids may be derived from naturally occurring fatty acids having at least one hydroxyl functionality, such as ricinoleic acid. Furthermore, the surfactants employed in the present invention or the fatty acids from which they are derived may be chemically or enzymatically modified so as to contain at least one hydroxyl functionality.

The fatty acid salts may be derived from fatty acids found, for example, in animals, plants or bacteria. The polar —COOH group on short-chain fatty acids (e.g., 2-4 carbon atoms) and even medium-chain (e.g., 6 to 10 carbon atoms) is typically enough to make them soluble in water. However, as chain length increases (e.g., from 14 to 25 carbons), the fatty acid type becomes progressively less water soluble and tends to take on oily or fatty characteristics. The presence of a hydroxy group on long-chain fatty acids increases water solubility. Therefore, water-soluble salts of hydroxy fatty acids having from 14 to 25 carbon atoms are useful in the compositions of the present invention. In particular, the water solubility of a hydroxy fatty acid salt allows it to solubilize an established stain into the saliva and loosens it so that it can be easily removed by chewing, brushing or saliva.

In some embodiments, the inventive oral compositions can include other anionic or nonionic surfactants. For example, other suitable surfactants may include the following anionic or non-ionic surfactants: sulfated butyl oleate, sodium oleate, salts of fumaric acid, potassium glomate, organic acid esters of mono- and diglycerides, stearyl monoglyceridyl citrate, succistearin, dioctyl sodium sulfosuccinate, glycerol tristearate, lecithin, hydroxylated lecithin, sodium lauryl sulfate, acetylated monoglycerides, succinylated monoglycerides, monoglyceride citrate, ethoxylated mono- and diglycerides, sorbitan monostearate, calcium stearyl-2-lactylate, sodium stearyl lactylate, lactylated fatty acid esters of glycerol and propylene glycol, glycerol-lactoesters of $C_8$-$C_{24}$ fatty acids, polyglycerol esters of $C_8$-$C_{24}$ fatty acids, propylene glycol alginate, sucrose $C_8$-$C_{24}$ fatty acid esters, diacetyl tartaric and citric acid esters of mono- and diglycerides, triacetin, sarcosinate surfactants, isethionate surfactants, tautate surfactants, pluronics, polyethylene oxide condensates of alkyl phenols, products derived from the condensation of ethylene oxide with the reaction product of propylene oxide and ethylene di amine, ethylene oxide condensates of aliphatic alcohols, long chain tertiary amine oxides, long chain tertiary phosphine oxides, long chain dialkyl sulfoxides and mixtures thereof.

The surfactant, alone or in combination with other surfactants, may be present in oral compositions of the present invention in concentrations of about 0.001% to about 20% by weight of the total composition. In some embodiments, the surfactant may be present at about 0.05 to about 10% by weight of the total composition. Moreover, in some embodiments, the surfactant may be present in amounts of about 0.05 to about 2% by weight of the total composition.

In some embodiments, the surfactant employed in the compositions of the present invention is sodium stearate, sodium ricinolente, a sodium lauryl sulfate, or a combination of these.

Anticalculus Agents

As described above, the oral compositions of the present invention may include encapsulated anticalculus active(s). These agents may be chelating agents that strongly interact with metal ions, such as the calcium found in the cell walls of mouth bacteria. Anticalculus agents can also disrupt plaque by removing calcium from the calcium bridges which help hold this biomass intact.

One group of agents suitable for use as anticalculus agents in the compositions of the present invention are phosphate salts. In some embodiments, the phosphate salt selected from the following: pyrophosphates, triphosphates, polyphosphates, polyphosphonates and combinations thereof. The anticalculus agent can be a dialkali metal pyrophosphate salt, a tetra alkali polyphosphate salt or a combination thereof. For example, in some embodiments, the chelating agent can be selected from the following: tetrasodium pyrophosphate, tetrapotassium pyrophosphate, sodium tripolyphosphate, sodium hexametaphosphate and combinations of these.

In some embodiments, the at least one encapsulated active is sodium hexametaphosphate. In further embodiments, the at least one encapsulated active is sodium tripolyphosphate.

Other anticalculus agents that can be employed in the compositions of the present invention may include tartaric acid and salts thereof, citric acid and alkali metal citrates and mixtures thereof.

In some embodiments, the anticalculus agent is present in amounts of about 0.001 to about 5% by weight of the inventive oral composition. Furthermore, in some embodiments, the anticalculus agent is present in amounts of about 0.5 to about 3% by weight of the oral composition.

Taste Masking Agents

In some embodiments, the encapsulated active is a taste masking agent. It may be useful to include a taste masking agent in oral compositions, which include unpleasant tasting compounds, such as bitter and/or metal tasting compounds. For example, as described above, polyphosphates can have a bitter taste. By encapsulating the polyphosphate in a suitable polymer matrix along with a taste masking agent, the bitter taste can be masked.

Examples of taste masking agents include high intensity sweeteners, hydrogenated castor oil, Cremophor RH40 from BASF, sodium citrate, acid salts, cherry flavor, fruit flavors, flavors Cremophor, and cooling compounds, for example. Taste masking agents may be employed in amounts of about 0.1% to about 7% by weight of the oral composition.

Oral Cleaning Agents (e.g. Enzymes)

In some embodiments, the oral compositions of the present invention include encapsulated oral cleaning agents. Suitable oral cleaning agents include enzymes, which are hydrolytic agents. Enzymes function to whiten teeth by removing the plaque and calculus that entrap dental stains. For example, a protease, lipase, amylase, glucoamylase, dextranase, mutanase, or glucose oxidase may be included in the invention compositions.

In some embodiments, the enzyme is present in amounts of about 0.01% to about 5.0% of the inventive oral composition. Furthermore, in some embodiments, the enzyme is present in amounts of about 0.01% to about 3.0%, or more specifically from about 0.1% to about 1.0% by weight of the oral composition.

Bleaching or Whitening Agents

The oral compositions of the present invention may include encapsulated bleaching or whitening agents. Suitable bleaching or whitening agents include peroxide compounds. Peroxides are believed to whiten teeth by releasing hydroxyl radicals capable of breaking down the plaque-stain complex into a form that can be flushed away or removed by abrasives. Useful peroxides should contain an 0-0 bond, which can break down to provide at least one active specie. Examples of preferred peroxide compounds are inorganic peroxides, such as hydrogen peroxide, calcium peroxide, strontium peroxide, zinc peroxide or magnesium peroxide, and organic peroxides including, but not limited to, carbamide peroxide.

The amount of the peroxide compound incorporated into the present composition will vary depending upon the particular individual or combinations of stain removing agents employed and the type of other components or components of the compositions and their respective amounts. The peroxide compound may be present in a stain removing effective amount of from about 0.01% to 10%, preferably from about 0.1% to 5%, and more preferably from about 0.2% to 3% by weight based on the total weight of the composition.

Sweetening Agents

In some embodiments, the oral compositions of the present invention include encapsulated sweetening agents, such as high intensity sweeteners. High intensity sweeteners include sucralose, aspartame, neotame, salts of acesulfame, and the like. In particular, it is common to employ such sugar substitutes in oral care compositions, such as tooth whitening gum compositions. Such high intensity sweeteners are desirably present in amounts up to about 1.0% by weight of the oral composition.

Other suitable sweeteners, which may be encapsulated, are the same as those described below.

Abrasive Agents

In some embodiments, the oral compositions of the present invention may include an encapsulated abrasive agent. Suitable abrasives include silicas, aluminas, phosphates, carbonates and combinations thereof. In some embodiments, the abrasive agent is a silica selected from: precipitated silica, silica gels and combinations thereof. Moreover, in some embodiments the abrasive agent is selected from the following: calcium carbonate, sodium bicarbonate, sodium metaphosphate, potassium metaphosphate, tricalcium phosphate, dehydrated dicalcium phosphate and combinations thereof. In some embodiments, the abrasive agent is sodium bicarbonate, which can also be considered an anticalculus.

The abrasive polishing material contemplated for use in the compositions of the present invention can be any material which does not excessively abrade dentin. However, silica dental abrasives have unique benefits of exceptional dental cleaning and polishing performance without unduly abrading tooth enamel or dentin.

The silica abrasive polishing materials herein, as well as other abrasives, generally have an average particle size ranging between about 0.1 to about 30 microns, and preferably from about 5 to about 15 microns. The abrasive can be precipitated silica or silica gels such as the silica xerogels described in U.S. Pat. No. 3,538,230 to Pader, et al. and U.S. Pat. No. 3,862,307 to DiGiulio, both incorporated herein by reference in their entirety. Preferred are the silica xerogels marketed under the trade name "Syloid" by the W. R. Grace & Company, Davison Chemical Division. Also preferred are the precipitated silica materials, such as those marketed by the J. M. Huber Corporation under the trade name "Zeodent", particularly the silica carrying the designation "Zeodent 119". The types of silica dental abrasives useful in the present invention are described in detail in U.S. Pat. No. 4,340,583 to Wason, incorporated herein by reference in its entirety. Silica abrasives described in U.S. patent application Ser. Nos.

08/434,147 and 08/434,149, both filed May 2, 1995, are also herein incorporated by reference.

In some embodiments, an abrasive is present in amounts from about 0.1 to about 30% by weight of the oral composition. The abrasive agent may be more typically employed in amounts from about 0.5 to about 5% by weight of the total composition. The abrasive in the toothpaste compositions of this invention is generally present at a level of from about 0.5% to about 10% by weight of the composition. Moreover, inventive chewing gum may contain from about 1% to about 6% of abrasive, by weight of the oral composition.

The silica used to prepare a chewing gum composition of the present invention is differentiated by means of its oil absorption value, having oil absorption value of less than 100 cc/100 g, and preferably in the range of from 45 cc/100 g silica to less than 70 cc/100 g silica. Silica particularly useful in the practice of the present invention is marketed under the trade designation SYLODENT XWA GRACE Davison Co., Columbia, DS 21044. An example of such silica is SYLODENT XWA 150, a silica precipitate having a water content of 4.7% by weight averaging from about 7 to about 11 microns in diameter, having an Einlehner Hardness of 5, a BET surface area of 390 $m^2/g$ of silica, an oil absorption of less than 70 $cm^3/100$ g of silica. This silica exhibits low abrasiveness to tooth enamel.

A silica abrasive can be used as the sole abrasive in preparing a chewing gum of the present invention or in combination with other known abrasives or polishing agents, including calcium carbonate, sodium bicarbonate, sodium metaphosphate, potassium metaphosphate, tricalcium phosphate, dehydrated dicalcium phosphate, or other siliceous materials, or combinations thereof.

In some embodiments, the total quantity of abrasive silica present in a chewing gum composition of the present invention is at a concentration of from about 0.1 to about 20% by weight. Moreover, in some embodiments, the total quantity of abrasive silica present in a chewing gum composition of the present invention is from about 0.5% to about 5% by weight.

Antibacterial Agents

In some embodiments, the oral compositions of the present invention include at least one encapsulated antibacterial agent. The antibacterial agent may be, but is not limited to, the following: triclosan, chlorhexidine, zinc citrate, silver nitrate, copper and cetylpyridinium chloride.

In some embodiments, the antibacterial agent is present in an oral composition of the present invention at a concentration of from about 0.01% to about 3.0% by weight.

Anticaries Agent

In still other embodiments, the oral compositions of the present invention include at least one encapsulated anticaries agent. An anticaries agent for use in the present invention may be a fluoride ion or a fluoride-providing component. Desirably, the anticaries agent would be useful in an amount sufficient to supply about 1 ppm to about 1,500 ppm of fluoride ions.

Anticaries agents include inorganic fluoride salts, such as soluble alkali metal salts. Examples include sodium fluoride, potassium fluoride, sodium fluorosilicate, ammonium fluorosilicate, and sodium monofluorophosphate. Suitable anticaries agents further include tin fluorides, such as stannous fluoride and stannous chloride. In one embodiment, sodium fluoride is a preferred anticaries agent.

A fluoride-containing compound having a beneficial effect on the care and hygiene of the oral cavity, e.g., diminution of enamel solubility in acid and protection of the teeth against decay, may also be incorporated encapsulated. Examples of fluoride-containing compounds, which would be suitable in this regard include sodium fluoride, stannous fluoride, potassium fluoride, potassium stannous fluoride, sodium hexafluorostannate, stannous chlorofluoride, sodium fluorozirconate and sodium monofluorophosphate. These materials, which disassociate or release fluoride-containing ions in water, suitably may be present in an effective, but not toxic amount, usually within the range of about 0.01 to about 1.0% by weight of the water-soluble fluoride content thereof.

Other anticaries agents may include xylitol and calcium casein peptone-calcium phosphate (CCP-CP).

Agents to Counter Breath Odor/Breath Freshening Agents

In some embodiments, the oral compositions of the present invention include at least one encapsulated agent to counter breath odor or freshen breath. These agents may be present in an oral composition of this invention an amount of about 0.01% to about 7.0% by weight.

Such agents include, for example, an essential oil, a flavoring aldehyde, or an alcohol. Examples of essential oils include oils of spearmint, peppermint, wintergreen, sassafras chlorophyll, clove, sage, eucalyptus, marjoram, cinnamon, lemon, lime, grapefruit and orange. Also useful are menthol, carvone and anethole. Of these, the most commonly employed are oils of peppermint, spearmint and chlorophyll. Other suitable flavoring agents are the same as those described below.

Suitable agents to counter breath odor or freshening breath also include the following: zinc citrate, zinc acetate, zinc fluoride, zinc ammonium sulfate, zinc bromide, zinc iodide, zinc chloride, zinc nitrate, zinc fluosilicate, zinc gluconate, zinc tartarate, zinc succinate, zinc formate, zinc chromate, zinc phenol sulfonate, zinc dithionate, zinc sulfate, silver nitrate, zinc salicylate, zinc glycerophosphate, copper nitrate and combinations thereof.

Other Active Components

In some embodiments, the at least one encapsulated active component is a desensitizing agent. The desensitizing agent may be, for example, potassium nitrate or potassium citrate.

In other embodiments, the at least one encapsulated active component is a dental remineralization agent. For example, the dental remineralization agent may be calcium casein peptone-calcium phosphate (CCP-CP) or calcium phosphates casein glycomacropeptide.

In further embodiments, the encapsulated active component is a plaque buffering agent, an example of which is urea.

In still other embodiments, the encapsulated active component may be a cooling agent or warming agent. Suitable examples, and their amounts are provided below.

In yet still other embodiments, the encapsulated active may be an herbal agent, a medicament or a vitamin.

Carrier Composition

The oral compositions of the present invention include a carrier composition, in an appropriate amount to accommodate the other components of the formulation. The term "carrier composition" refers to a vehicle capable of being mixed with the encapsulated active components for delivery to the oral cavity for oral care purposes, and which will not cause harm to warm-blooded animals, including humans. The carriers further include those components of the composition that are capable of being commingled without interaction in a manner which would substantially reduce the composition's stability and/or efficacy for dental stain-removal in the oral cavity of warm-blooded animals, including humans, in accordance with the compositions and methods of the present invention.

The carriers of the present invention can include one or more compatible solid or liquid filler diluents or encapsulating substances, which are suitable for oral administration.

The carriers or excipients employed in the present invention may be in any form appropriate to the mode of delivery, for example, solutions, colloidal dispersions, emulsions, suspensions, rinses, gels, foams, powders, solids, and the like, and can include conventional components of toothpastes (including gels), mouthwashes and rinses, mouth sprays, chewing gums, lozenges, and confectionaries. Carriers suitable for the preparation of compositions of the present invention are well known in the art. Their selection will depend on secondary considerations like taste, cost, shelf stability and the like.

In some embodiments, an oral composition of the present invention includes a carrier composition selected from the following: a gum base, a confectionary base, a toothpaste base, a gel dentifrice base and a tooth powder base. For example, the oral composition may be a gum composition, lozenge composition, mint composition, candy composition, toothpaste composition, gel dentifrice composition, mouth rinse or mouthwash composition, or a toothpowder composition.

Types of additives or ingredients, which may be included in the present compositions include one or more desirable stain-removing agents as provided herein. The inventive compositions may also include a component selected from the following: elastomers, elastomer solvents, waxes, emulsifiers, plasticizers, softeners, dispersing agents, sweeteners, flavorants, humectants, active agents, cooling agents, warming agents, tooth whitening agents, colorants, bulking agents, fillers and combinations thereof.

Moreover, in some embodiments a film-forming polymer may be included in the compositions of the present invention. For example, the film-forming polymer may be a synthetic anionic polymeric polycarboxylate (SAPP), such a PVM/MA copolymer (Gantrez S-97, GAF Corp.). Such polymers are described in U.S. Pat. Nos. 5,334,375 and 5,505,933, which are incorporated by reference herein in their entirety. SAPP's have previously been described as being useful for dentin sensitivity reduction. Moreover, SAPP's have previously been described as antibacterial-enhancing agents, which enhance delivery of an antibacterial agent to oral surfaces, and which enhance the retention of the antibacterial agent on oral surfaces. It is well within the contemplation of the present invention that film-forming polymers, such as PVM/MA copolymer, may be employed in the compositions of the present invention as a means of reducing stain formation.

As described above, in some embodiments, the inventive composition may be a gum composition including a gum base and the encapsulated active.

As described above, in some embodiments, the inventive composition may be a gum composition including a gum base and the encapsulated active. The gum base may be present in an amount of about 20 to about 40% by weight of the total composition. It may include any component known in the chewing gum art. For example, the gum base may include sweeteners, elastomers, bulking agents, waxes, elastomer solvents, emulsifiers, plasticizers, fillers, mixtures thereof and may include a desirable oral care agent(s) as provided herein.

In some embodiments, the gum base may include a suitable sugar bulking agent. For example, the gum base may include a specific polyol composition including at least one polyol which is from about 30% to about 80% by weight of the gum base, and desirably from 50% to about 60%. The polyol composition may include any polyol known in the art including, but not limited to maltitol, sorbitol, erythritol, xylitol, mannitol, isomalt, lactitol and combinations thereof. Lycasin which is a hydrogenated starch hydrolysate including sorbitol and maltitol, may also be used.

The elastomers (rubbers) employed in the gum base will vary greatly depending upon various factors such as the type of gum base desired, the consistency of gum composition desired and the other components used in the composition to make the final chewing gum product. The elastomer may be any water-insoluble polymer known in the art, and includes those gum polymers utilized for chewing gums and bubble gums. Illustrative examples of suitable polymers in gum bases include both natural and synthetic elastomers. For example, those polymers which are suitable in gum base compositions include, without limitation, natural substances (of vegetable origin) such as chicle, natural rubber, crown gum, nispero, rosidinha, jelutong, perillo, niger gutta, tunu, balata, guttapercha, lechi capsi, sorva, gutta kay, and the like, and mixtures thereof. Examples of synthetic elastomers include, without limitation, styrene-butadiene copolymers (SBR), polyisobutylene, isobutylene-isoprene copolymers, polyethylene, polyvinyl acetate and the like, and mixtures thereof.

The amount of elastomer employed in the gum base may vary depending upon various factors such as the type of gum base used, the consistency of the gum composition desired and the other components used in the composition to make the final chewing gum product. In general, the elastomer will be present in the gum base in an amount from about 10% to about 60% by weight of the gum region, desirably from about 35% to about 40% by weight.

When a wax is present in the gum base, it softens the polymeric elastomer mixture and improves the elasticity of the gum base. The waxes employed will have a melting point below about 60° C., and preferably between about 45° C. and about 55° C. The low melting wax may be a paraffin wax. The wax may be present in the gum base in an amount from about 6% to about 10%, and preferably from about 7% to about 9.5%, by weight of the gum base.

In addition to the low melting point waxes, waxes having a higher melting point may be used in the gum base in amounts up to about 5%, by weight of the gum base. Such high melting waxes include beeswax, vegetable wax, candelilla wax, carnuba wax, most petroleum waxes, and the like, and mixtures thereof.

In addition to the components set out above, the gum base may include a variety of other components, such as components selected from elastomer solvents, emulsifiers, plasticizers, fillers, and mixtures thereof.

The gum base may contain elastomer solvents to aid in softening the elastomer component. Such elastomer solvents may include those elastomer solvents known in the art, for example, terpinene resins such as polymers of alpha-pinene or beta-pinene, methyl, glycerol and pentaerythritol esters of rosins and modified rosins and gums such as hydrogenated, dimerized and polymerized rosins, and mixtures thereof. Examples of elastomer solvents suitable for use herein may include the pentaerythritol ester of partially hydrogenated wood and gum rosin, the pentaerythritol ester of wood and gum rosin, the glycerol ester of wood rosin, the glycerol ester of partially dimerized wood and gum rosin, the glycerol ester of polymerized wood and gum rosin, the glycerol ester of tall oil rosin, the glycerol ester of wood and gum rosin and the partially hydrogenated wood and gum rosin and the partially hydrogenated methyl ester of wood and rosin, and the like, and mixtures thereof. The elastomer solvent may be employed in the gum base in amounts from about 2% to about 15%, and preferably from about 7% to about 1%, by weight of the gum base.

The gum base may also include emulsifiers which aid in dispersing any immiscible components into a single stable system. The emulsifiers useful in this invention include glyceryl monostearate, lecithin, fatty acid monoglycerides, diglycerides, propylene glycol monostearate, and the like, and mixtures thereof. The emulsifier may be employed in amounts from about 2% to about 15%, and more specifically, from about 7% to about 1%, by weight of the gum base.

The gum base may also include plasticizers or softeners to provide a variety of desirable textures and consistency properties. Because of the low molecular weight of these components, the plasticizers and softeners are able to penetrate the fundamental structure of the gum base making it plastic and less viscous. Useful plasticizers and softeners include lanolin, palmitic acid, oleic acid, stearic acid, sodium stearate, potassium stearate, glyceryl triacetate, glyceryl lecithin, glyceryl monostearate, propylene glycol monostearate, acetylated monoglyceride, glycerine, and the like, and mixtures thereof. Waxes, for example, natural and synthetic waxes, hydrogenated vegetable oils, petroleum waxes such as polyurethane waxes, polyethylene waxes, paraffin waxes, microcrystalline waxes, fatty waxes, sorbitan monostearate, tallow, propylene glycol, mixtures thereof, and the like, may also be incorporated into the gum base. The plasticizers and softeners are generally employed in the gum base in amounts up to about 20% by weight of the gum base, and more specifically in amounts from about 9% to about 17%, by weight of the gum base.

Plasticizers also include are the hydrogenated vegetable oils and include soybean oil and cottonseed oil which may be employed alone or in combination. These plasticizers provide the gum base with good texture and soft chew characteristics. These plasticizers and softeners are generally employed in amounts from about 5% to about 14%, and more specifically in amounts from about 5% to about 13.5%, by weight of the gum base.

Anhydrous glycerin may also be employed as a softening agent, such as the commercially available United States Pharmacopeia (USP) grade. Glycerin is a syrupy liquid with a sweet warm taste and has a sweetness of about 60% of that of cane sugar. Because glycerin is hygroscopic, the anhydrous glycerin may be maintained under anhydrous conditions throughout the preparation of the chewing gum composition.

Although softeners may be present to modify the texture of the gum composition, they may be present in reduced amounts as compared to typical gum compositions. For example, they may be present from about 0.5 to about 10% by weight based on the total weight of the composition, or they may not be present in the composition, since a surfactant active can act as a softener.

The gum base of this invention may also include effective amounts of bulking agents such as mineral adjuvants, which may serve as fillers and textural agents. Useful mineral adjuvants include calcium carbonate, magnesium carbonate, alumina, aluminum hydroxide, aluminum silicate, talc, tricalcium phosphate, dicalcium phosphate, calcium sulfate and the like, and mixtures thereof. These fillers or adjuvants may be used in the gum base compositions in various amounts. Preferably the amount of filler, when used, will be present in an amount from about 15% to about 40%, and desirably from about 20% to about 30%, by weight of the gum base.

A variety of traditional additives may be optionally included in the gum base in effective amounts such as coloring agents, antioxidants, preservatives, flavoring agents, and the like. For example, titanium dioxide and other dyes suitable for food, drug and cosmetic applications, known as F. D. & C. dyes, may be utilized. An anti-oxidant such as butylated hydroxytoluene (BHT), butylated hydroxyanisole (BHA), propyl gallate, and mixtures thereof, may also be included.

Other conventional chewing gum additives known to one having ordinary skill in the chewing gum art may also be used in the gum base.

Some embodiments extend to methods of making the gum compositions. The manner in which the gum base components are mixed is not critical and is performed using standard techniques and apparatus known to those skilled in the art. In a typical method, an elastomer is admixed with an elastomer solvent and/or a plasticizer and/or an emulsifier and agitated for a period of from 1 to 30 minutes. The remaining components, such as the low melting point wax, are then admixed, either in bulk or incrementally, while the gum base mixture is blended again for 1 to 30 minutes.

The gum composition may include amounts of conventional additives selected from, but not limited to, the following: sweetening agents (sweeteners), plasticizers, softeners, emulsifiers, waxes, fillers, bulking agents (carriers, extenders, bulk sweeteners), mineral adjuvants, flavoring agents (flavors, flavorings), coloring agents (colorants, colorings), antioxidants, acidulants, thickeners, medicaments, and the like, and mixtures thereof. Some of these additives may serve more than one purpose. For example, in sugarless gum compositions, a sweetener, such as maltitol or other sugar alcohol, may also function as a bulking agent.

The plasticizers, softening agents, mineral adjuvants, waxes and antioxidants discussed above, as being suitable for use in the gum base, may also be used in the chewing gum composition. Examples of other conventional additives which may be used include emulsifiers, such as lecithin and glyceryl monostearate, thickeners, used alone or in combination with other softeners, such as methyl cellulose, alginates, carrageenan, xanthan gum, gelatin, carob, tragacanth, locust bean, and carboxy methyl cellulose, acidulants such as malic acid, adipic acid, citric acid, tartaric acid, fumaric acid, and mixtures thereof, and fillers, such as those discussed above under the category of mineral adjuvants.

In some embodiments, the gum region may also contain a bulking agent. Suitable bulking agents may be water-soluble and include sweetening agents selected from, but not limited to, monosaccharides, disaccharides, polysaccharides, sugar alcohols, and mixtures thereof; randomly bonded glucose polymers such as those polymers distributed under the tradename POLYDEXTROSE by Pfizer, Inc., Groton, Conn.; isomalt (a racemic mixture of alpha-D-glucopyranosyl-1,6-mannitol and alpha-D-glucopyranosyl-1,6-sorbitol manufactured under the tradename PALATINIT by Suddeutsche Zucker), maltodextrins; hydrogenated starch hydrolysates; hydrogenated hexoses; hydrogenated disaccharides; minerals, such as calcium carbonate, talc, titanium dioxide, dicalcium phosphate; celluloses; and mixtures thereof.

Suitable sugar bulking agents include monosaccharides, disaccharides and polysaccharides such as xylose, ribulose, glucose (dextrose), mannose, galactose, fructose (levulose), sucrose (sugar), maltose, invert sugar, partially hydrolyzed starch and corn syrup solids, and mixtures thereof.

Suitable sugar alcohol bulking agents include sorbitol, xylitol, mannitol, galactitol, maltitol, and mixtures thereof.

Suitable hydrogenated starch hydrolysates include those disclosed in U.S. Pat. Nos. 25,959, 3,356,811, 4,279,931 and various hydrogenated glucose syrups and/or powders which contain sorbitol, hydrogenated disaccharides, hydrogenated higher polysaccharides, or mixtures thereof. Hydrogenated starch hydrolysates are primarily prepared by the controlled catalytic hydrogenation of corn syrups. The resulting hydrogenated starch hydrolysates are mixtures of monomeric, dimeric, and polymeric saccharides. The ratios of these different saccharides give different hydrogenated starch hydrolysates different properties. Mixtures of hydrogenated starch hydrolysates, such as LYCASIN, a commercially available product manufactured by Roquette Freres of France, and HYSTAR, a commercially available product manufactured by Lonza, Inc., of Fairlawn, N.J., are also useful.

The sweetening agents used may be selected from a wide range of materials including water-soluble sweeteners, water-soluble artificial sweeteners, water-soluble sweeteners derived from naturally occurring water-soluble sweeteners, dipeptide based sweeteners, and protein based sweeteners, including mixtures thereof. Without being limited to particular sweeteners, representative categories and examples include:

(a) water-soluble sweetening agents such as dihydrochalcones, monellin, steviosides, glycyrrhizin, dihydroflavenol, and sugar alcohols such as sorbitol, mannitol, maltitol, and L-aminodicarboxylic acid aminoalkenoic acid ester amides, such as those disclosed in U.S. Pat. No. 4,619,834, which disclosure is incorporated herein by reference, and mixtures thereof;

(b) water-soluble artificial sweeteners such as soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (Acesulfame-K), the free acid form of saccharin, and mixtures thereof;

(c) dipeptide based sweeteners, such as L-aspartic acid derived sweeteners, such as L-aspartyl-L-phenylalanine methyl ester (Aspartame), N-[N-(3,3-dimethylbutyl)-L-α-aspartyl]-L-phenylalanine 1-methyl ester (Neotame), and materials described in U.S. Pat. No. 3,492,131, L-alphaaspartyl-N-(2,2,4,4-tetramethyl-3-thietanyl)-D-alaninamide hydrate (Alitame), methyl esters of L-aspartyl-L-phenylglycerine and L-aspartyl-L-2,5-dihydrophenyl-glycine, L-aspartyl-2,5-dihydro-L-phenylalanine; L-aspartyl-L-(1-cyclohexen)-alanine, and mixtures thereof;

(d) water-soluble sweeteners derived from naturally occurring water-soluble sweeteners, such as chlorinated derivatives of ordinary sugar (sucrose), e.g., chlorodeoxysugar derivatives such as derivatives of chlorodeoxysucrose or chlorodeoxygalactosucrose, known, for example, under the product designation of Sucralose; examples of chlorodeoxysucrose and chlorodeoxygalactosucrose derivatives include but are not limited to: 1-chloro-1'-deoxysucrose; 4-chloro-4-deoxy-alpha-D-galactopyranosyl-alpha-D-fructofuranoside, or 4-chloro-4-deoxygalactosucrose; 4-chloro-4-deoxy-alpha-D-galactopyranosyl-1-chloro-1-deoxy-beta-D-fructo-furanoside, or 4,1'-dichloro-4,1'-dideoxygalactosucrose; 1',6'-dichloro1',6'-dideoxysucrose; 4-chloro-4-deoxy-alpha-D-galactopyranosyl-1,6-dichloro-1,6-dideoxy-beta-D-fructofuranoside, or 4,1',6'-trichloro-4,1',6'-trideoxygalactosucrose; 4,6-dichloro-4,6-dideoxy-alpha-D-galactopyranosyl-6-chloro-6-deoxy-beta-D-fructofuranoside, or 4,6,6'-trichloro-4,6,6'-trideoxygalactosucrose; 6,1',6'-trichloro-6,1',6'-trideoxysucrose; 4,6-dichloro-4,6-dideoxy-alpha-D-galacto-pyranosyl-1,6-dichloro-1,6-dideoxy-beta-D-fructofuranoside, or 4,6,1',6'-tetrachloro4,6,1',6'-tetradeoxygalacto-sucrose; and 4,6,1',6'-tetradeoxysucrose, and mixtures thereof; and (e) protein based sweeteners such as thaumaoccous danielli (Thaumatin I and II).

The intense sweetening agents may be used in many distinct physical forms well-known in the art to provide an initial burst of sweetness and/or a prolonged sensation of sweetness. Without being limited thereto, such physical forms include free forms, such as spray dried, powdered, beaded forms, encapsulated forms, and mixtures thereof.

Desirably, the sweetener is a high intensity sweetener such as aspartame, sucralose, and acesulfame potassium (Ace-K).

In general, an effective amount of sweetener may be utilized to provide the level of sweetness desired, and this amount may vary with the sweetener selected. The amount of sweetener may be present in amounts from about 0.001% to about 3%, by weight of the gum composition, depending upon the sweetener or combination of sweeteners used. The exact range of amounts for each type of sweetener may be selected by those skilled in the art.

The flavoring agents which may be used include those flavors known to the skilled artisan, such as natural and artificial flavors. These flavorings may be chosen from synthetic flavor oils and flavoring aromatics and/or oils, oleoresins and extracts derived from plants, leaves, flowers, fruits, and so forth, and combinations thereof. Nonlimiting representative flavor oils include spearmint oil, cinnamon oil, oil of wintergreen (methyl salicylate), peppermint oil, clove oil, bay oil, anise oil, eucalyptus oil, thyme oil, cedar leaf oil, oil of nutmeg, allspice, oil of sage, mace, oil of bitter almonds, and cassia oil. Also useful flavorings are artificial, natural and synthetic fruit flavors such as vanilla, and citrus oils including lemon, orange, lime, grapefruit, and fruit essences including apple, pear, peach, grape, strawberry, raspberry, cherry, plum, pineapple, apricot and so forth. These flavoring agents may be used in liquid or solid form and may be used individually or in admixture. Commonly used flavors include mints such as peppermint, menthol, spearmint, artificial vanilla, cinnamon derivatives, and various fruit flavors, whether employed individually or in admixture.

Other useful flavorings include aldehydes and esters such as cinnamyl acetate, cinnamaldehyde, citral diethylacetal, dihydrocarvyl acetate, eugenyl formate, p-methylamisol, and so forth may be used. Generally any flavoring or food additive such as those described in Chemicals Used in Food Processing, publication 1274, pages 63-258, by the National Academy of Sciences, may be used. This publication is incorporated herein by reference.

Further examples of aldehyde flavorings include but are not limited to acetaldehyde (apple), benzaldehyde (cherry, almond), anisic aldehyde (licorice, anise), cinnamic aldehyde (cinnamon), citral, i.e., alpha-citral (lemon, lime), neral, i.e., beta-citral (lemon, lime), decanal (orange, lemon), ethyl vanillin (vanilla, cream), heliotrope, i.e., piperonal (vanilla, cream), vanillin (vanilla, cream), alpha-amyl cinnamaldehyde (spicy fruity flavors), butyraldehyde (butter, cheese), valeraldehyde (butter, cheese), citronellal (modifies, many types), decanal (citrus fruits), aldehyde C-8 (citrus fruits), aldehyde C-9 (citrus fruits), aldehyde C-12 (citrus fruits), 2-ethyl butyraldehyde (berry fruits), hexenal, i.e., trans-2 (berry fruits), tolyl aldehyde (cherry, almond), veratraldehyde (vanilla), 2,6-dimethyl-5-heptenal, i.e., melonal (melon), 2,6-dimethyloctanal (green fruit), and 2-dodecenal (citrus, mandarin), cherry, grape, strawberry shortcake, and mixtures thereof.

In some embodiments, the flavoring agent may be employed in either liquid form and/or dried form. When employed in the latter form, suitable drying means such as spray drying the oil may be used. Alternatively, the flavoring agent may be absorbed onto water soluble materials, such as cellulose, starch, sugar, maltodextrin, gum arabic and so forth or may be encapsulated. The actual techniques for preparing such dried forms are well-known.

In some embodiments, the flavoring agents may be used in many distinct physical forms well-known in the art to provide an initial burst of flavor and/or a prolonged sensation of flavor. Without being limited thereto, such physical forms include free forms, such as spray dried, powdered, beaded forms, encapsulated forms, and mixtures thereof.

The amount of flavoring agent employed herein may be a matter of preference subject to such factors as the type of final chewing gum composition, the individual flavor, the gum base employed, and the strength of flavor desired. Thus, the amount of flavoring may be varied in order to obtain the result desired in the final product and such variations are within the capabilities of those skilled in the art without the need for undue experimentation. In gum compositions, the flavoring agent is generally present in amounts from about 0.02% to about 5%, and more specifically from about 0.1% to about 2%, and even more specifically, from about 0.8% to about 1.8%, by weight of the chewing gum composition.

Coloring agents may be used in amounts effective to produce the desired color. The coloring agents may include pigments which may be incorporated in amounts up to about 6%, by weight of the gum composition. For example, titanium dioxide may be incorporated in amounts up to about 2%, and preferably less than about 1%, by weight of the gum composition. The colorants may also include natural food colors and dyes suitable for food, drug and cosmetic applications. These colorants are known as F.D.& C. dyes and lakes. The materials acceptable for the foregoing uses are preferably water-soluble. Illustrative nonlimiting examples include the indigoid dye known as F.D.& C. Blue No. 2, which is the disodium salt of 5,5-indigotindisulfonic acid. Similarly, the dye known as F.D.& C. Green No. 1 comprises a triphenylmethane dye and is the monosodium salt of 4-[4-(N-ethyl-p-sulfoniumbenzylamino)diphenylmethylene]-[1-(N-ethyl-N-p-sulfoniumbenzyl)-delta-2,5-cyclohexadieneimine]. A full recitation of all F.D.& C. colorants and their corresponding chemical structures may be found in the Kirk-Othmer Encyclopedia of Chemical Technology, 3rd Edition, in volume 5 at pages 857-884, which text is incorporated herein by reference.

Suitable oils and fats usable in gum compositions include partially hydrogenated vegetable or animal fats, such as coconut oil, palm kernel oil, beef tallow, and lard, among others. These components when used are generally present in amounts up to about 7%, and preferably up to about 3.5%, by weight of the gum composition.

Some embodiments may include a method for preparing the gum compositions, including both chewing gum and bubble gum compositions. The chewing gum compositions may be prepared using standard techniques and equipment known to those skilled in the art. The apparatus useful in accordance with some embodiments comprises mixing and heating apparatus well known in the chewing gum manufacturing arts, and therefore the selection of the specific apparatus will be apparent to the artisan.

In some embodiments, a method of preparing a tooth whitening gum composition includes at least partially encapsulating at least one active component of the composition in a polymer matrix. In some embodiments, the polymer matrix may have a tensile strength of at least about 6,500 psi and/or may include at least one polymer having a water absorption of about 0.01% to about 50%. The method also includes heating a gum base to soften the base and then mixing the softened gum base with the at least partially encapsulated active component so as to obtain a substantially homogeneous mixture. The method further includes cooling the mixture and forming the cooled mixture into individual gum pieces. Further components may be mixed into the softened gum base. For example, one or more of the following may typically be added: bulking agent, filler, humectant, flavorant, colorant, dispersing agent, softener, plasticizer, preservative, warming agent, cooling agent, tooth whitening agent and sweetener.

In some desired embodiment, the method of preparing a gum composition of the present invention can involve combining at least one encapsulated active with a gum base. The encapsulation procedure may, in one desired embodiment, involve extrusion.

For example, as detailed in the examples below, an oral delivery system of the present invention may be prepared by first melting a suitable polymer, such as polyvinyl acetate (PVAC), in a high shear mixer. A hydrogenated oil may then be added to the molten polymer. The active ingredient may then be added to the resulting mixture and mixed under high shear. The resulting filled polymer melt is then cooled and ground to a suitable size (e.g., less than 590 microns). The encapsulated active matrix may be stored in an air tight container with low humidity until it is to be employed in a gum base.

In some other embodiments, the method of preparing a gum composition of the present invention can involve suspending tooth whitening active particles in a fluidized air stream; and spraying a coating onto the suspended active particles. In some embodiments, the coating may include at least one polymer having a water absorption of about 0.01% to about 50%. Moreover, in some embodiments, the polymer may have a tensile strength of at least about 6,500 psi in the oral delivery system. Suitable actives are the same as those described above. Moreover, suitable polymers are the same as those described above. One or more coating layers may be sprayed onto the suspended active particles. The coating composition sprayed on the particles may include any solvent. The encapsulated particles may be combined with a gum base, as described in the Examples Section The encapsulated particles of some embodiments may be prepared by any suitable spray coating method as known in the art. One suitable process is the Wurster process. This process provides a method for encapsulating individual particulate materials. First the particles to be encapsulated are suspended in a fluidizing air stream which provides a generally cyclic flow in front of a spray nozzle. The spray nozzle sprays an atomized flow of the coating solution.

The atomized barrier coating solution collides with the particles as they are carried away from the nozzle to provide a particle coating with the coating solution. The temperature of the fluidizing air stream, which also serves to suspend the particles to be coated, may be adjusted to evaporate the solvent shortly after the coating solution contacts the particles. This serves to solidify the coating on the particles, resulting in the desired encapsulated particle.

This process may be repeated until the desired thickness of the coating is achieved. Alternatively, the process may be repeated with a different coating solution to provide different and distinct coating layers in the encapsulated particle composition.

Following the coating process, the particles may then be formed to an appropriate size as desired, generally from an average particle size range of about 50 μm to about 800 μm. This may be accomplished by any suitable means such as chopping, pulverizing, milling or grinding the particles.

In some embodiments, gum pieces may be coated with an aqueous gum coating composition, which may be applied by any method known in the art. The gum coating composition may be present in an amount from about 25% to about 35% by weight of the total gum piece, more specifically about 30% by weight of the gum piece.

The outer gum coating may be hard or crunchy. Typically, the outer gum coating may include sorbitol, maltitol, xylitol, isomalt, and other crystallizable polyols; sucrose may also be used. Flavors may also be added to yield unique product characteristics. Moreover, the outer gum coating may include one or more of the encapsulated active agents provided herein.

The gum coating, if present, may include several opaque layers, such that the chewing gum composition is not visible through the coating itself, which can optionally be covered with a further one or more transparent layers for aesthetic, textural and protective purposes. The outer gum coating may also contain small amounts of water and gum arabic. The gum coating can be further coated with wax. The gum coating may be applied in a conventional manner by successive applications of a coating solution, with drying in between each coat. As the coating dries it usually becomes opaque and is usually white, though other colorants may be added. A polyol coating can be further coated with wax. The gum coating can further include colored flakes or speckles.

If the composition comprises a gum coating, it is possible that one or more oral care actives can be dispersed throughout the coating. This may be preferred if one or more oral care actives is incompatible in a single phase composition with another of the actives. Moreover, it is well within the contemplation of the present invention that providing one or more of the stain-removing agents in the gum coating can enhance the stain-removing efficacy of the total composition.

The encapsulated active can be included in one or more of the chewing gum regions such as the gum coating, the gum base or both. Additionally, the encapsulated active can be added at different stages of the manufacture, alone or as a premix with other components. For example, in some embodiments, the method for preparing a gum composition includes heating a gum base to soften the base; and mixing the softened gum base with at least one of the following: elastomer, wax, emulsifier, bulking agent, filler, humectant, flavorant, colorant, dispersing agent, softener, plasticizer, preservative, warming agent, cooling agent, encapsulated active agent and sweetener to obtain a substantially homogeneous mixture. The method also involves cooling the mixture; forming the cooled mixture into individual gum pieces; and coating the gum pieces with a gum coating solution including the encapsulated active. One or more other components may be included in the gum coating, such as including, but not limited to, the following: gum arabic, flavorant, colorant, sweetener, bulking agent, filler, anti-adherent compound, dispersing agent, moisture absorbing compound, warming agent, cooling agent and film-forming agent.

The gum coating may be formulated to assist with increasing the thermal stability of the gum piece and preventing leaking of a liquid fill if the gum product is a center-filled gum. In some embodiments, the gum coating may include a gelatin composition. The gelatin composition may be added as a 40% by weight solution and may be present in the gum coating composition from about 5% to about 10% by weight of the gum coating composition, and more specifically about 7% to about 8%. The gel strength of the gelatin may be from about 130 bloom to about 250 bloom.

Additives, such as physiological cooling agents, throat-soothing agents, spices, warming agents, tooth-whitening agents, breath-freshening agents, vitamins minerals, caffeine, drugs and other actives may be included in any or all portions of the chewing gum composition. Such components may be used in amounts sufficient to achieve their intended effects.

With respect to cooling agents, a variety of well known cooling agents may be employed. For example, among the useful cooling agents are included menthol, xylitol, menthane, menthone, menthyl acetate, menthyl salicylate, N,2,3-trimethyl-2-isopropyl butanamide (WS-23), N-ethyl-p-menthane-3-carboxamide (WS-3), menthyl succinate, 3,1-menthoxypropane 1,2-diol, among others. These and other suitable cooling agents are further described in the following U.S. patents, all of which are incorporated in their entirety by reference hereto: U.S. Pat. Nos. 4,230,688 and 4,032,661 to Rowsell et al.; U.S. Pat. No. 4,459,425 to Amano et al.; U.S. Pat. No. 4,136,163 to Watson et al.; and U.S. Pat. No. 5,266,592 to Grub et al. These cooling agents may be present in one or more of the outer gum coatings, the gum region surrounding the liquid fill, the liquid fill per se, or in any combination of those three gum areas. Cooling agents, when used in the outer coating composition for the gum, are generally present in amount of 0.01% to about 1.0%. When used in the other portions of the gum, such as the gum region or the center fill, they may be present in amounts of about 0.001 to about 10% by weight of the total chewing gum piece.

Warming components may be selected from a wide variety of compounds known to provide the sensory signal of warming to the user. These compounds offer the perceived sensation of warmth, particularly in the oral cavity, and often enhance the perception of flavors, sweeteners and other organoleptic components. Among the useful warming compounds included are vanillyl alcohol n-butylether (TK-1000) supplied by Takasago Perfumary Company Limited, Tokyo, Japan, vanillyl alcohol n-propylether, vanillyl alcohol isopropylether, vanillyl alcohol isobutylether, vanillyl alcohol n-aminoether, vanillyl alcohol isoamyleather, vanillyl alcohol n-hexyleather, vanillyl alcohol methylether, vanillyl alcohol ethyleather, gingerol, shogaol, paradol, zingerone, capsaicin, dihydrocapsaicin, nordihydrocapsaicin, homocapsaicin, homodihydrocapsaicin, ethanol, isopropol alcohol, iso-amylalcohol, benzyl alcohol, glycerine, and combinations thereof.

The features and advantages of the present invention are more fully shown by the following examples which are provided for purposes of illustration, and are not to be construed as limiting the invention in any way.

EXAMPLES

Example 1

Encapsulation of Sodium tripolyphosphate (STP)

An oral delivery system is prepared in the present example. The system includes sodium tripolyphosphate (STP) as the active component; and a polyvinylacetate matrix encapsulating the STP. The components of the delivery system are shown in Table 1.

TABLE 1

| Components | Wt. Percent |
| --- | --- |
| Polyvinyl Acetate | 52.00 |
| Hydrogenated Oil | 3.00 |
| STP | 45.00 |
| Total | 100 |

The procedure used to prepare the delivery system is as follows: Polyvinyl acetate is melted at a temperature of about 105° C. in a high shear mixer, such as an extruder (single or twin screw) or sigma or Banbury mixer. The hydrogenated oil is added to the molten polyvinyl acetate. Sodium tripolyphosphate (STP) is then added to the resulting mixture and mixed under high shear to completely disperse the ingredients. The resulting filled polymer melt is cooled and ground to a particle size of less than 590 microns. The encapsulated STP matrix is stored in air tight containers with low humidity below 35° C.

Example 2

Encapsulation of Sodium Tripolyphosphate (STP), Sodium Hexametaphosphate (SHMP) and Sucralose A further oral delivery system is prepared in the present example. The system includes STP, SHMP and sucralose as the active components. The system also includes a polyvinyl acetate matrix, which encapsulates the actives. The components of the delivery system are shown in Table 2.

TABLE 2

| Components | Wt. Percent |
| --- | --- |
| Polyvinyl Acetate | 62.00 |
| Hydrogenated Oil | 3.00 |
| STP | 20.00 |
| SHMP | 10.00 |
| Sucralose | 5.00 |
| Total | 100 |

The procedure used to prepare the delivery system is as follows: Polyvinyl acetate is melted at a temperature of about 85° C. in a high shear mixer, such as an extruder (single or twin screw) or sigma or Banbury mixer. The hydrogenated oil is then added to the molten polyvinyl acetate. STP, SHMP and sucralose are added to the resulting mixture and mixed under high shear to completely disperse the ingredients. The resulting filled polymer melt is cooled and ground to a particle size of less than 590 microns. The encapsulation is stored in air tight containers with low humidity below 35° C.

Example 3

Encapsulation of Sodium Tripolyphosphate, Sodium Stearate and Sucralose

Yet another oral delivery system is prepared in the present example. This system includes the following actives: STP, sodium stearate and sucralose. The system also includes polyvinyl acetate, which at least partially encapsulates the actives. The components of the delivery system are shown in Table 3.

TABLE 3

| Components | Wt. Percent |
| --- | --- |
| Polyvinyl Acetate | 57.00 |
| Hydrogenated Oil | 3.00 |
| STP | 20.00 |
| Sodium stearate | 15.00 |
| Sucralose | 5.00 |
| Total | 100 |

The procedure used to prepare the delivery system is as follows: Polyvinyl acetate is melted at a temperature of about 85° C. in a high shear mixer, such as an extruder (single or twin screw) or sigma or Banbury mixer. The hydrogenated oil is then added to the molten polyvinyl acetate. STP, sodium stearate and sucralose are added to the resulting mixture and mixed under high shear to completely disperse the ingredients. The resulting filled polymer melt is cooled and ground to a particle size of less than 590 microns. The encapsulation is stored in air tight containers with low humidity below 35° C.

Example 4

Chewing Gum Composition Including STP/Polyvinylacetate Encapsulation (From Example 1)

A chewing gum composition is prepared according to know procedures using the polyvinyl acetate encapsulated STP prepared in Example 1. The chewing gum components are shown in Table 4.

TABLE 4

| Components | Wt. Percent |
| --- | --- |
| Gum Base | 36.0 |
| Sorbitol | 53.8 |
| Glycerin | 1.0 |
| Flavor | 2.5 |
| Sodium tripolyphosphate/polyvinyl acetate encapsulation (from Example 1) | 6.7 |
| Total | 100 |

The chewing gum composition is prepared as follows. The gum base is melted at a suitable temperature in a mixer. The remaining components are then added to the melted gum base and mixed until the components are completely dispersed. The resulting chewing gum composition is sized.

Table 5 below shows the release of STP from chewing gums including encapsulated STP (composition of Table 4), as compared to the same gum composition including free STP. The % amount of STP remaining in the bolus was measured over a period of about 20 minutes. The results in Table 5 are presented graphically in FIG. 1.

TABLE 5

| | Chewing Time | | | | |
| --- | --- | --- | --- | --- | --- |
| | 0 Min. | 5 Min. | 10 Min. | 15 Min. | 20 Min. |
| Free STP | 100.0% | 20.3% | 2.0% | 1.3% | 0.0% |
| Encapsulated STP | 100.0% | 79.0% | 44.0% | 27.0% | 14.0% |

Based on the results in Table 5 (and FIG. 1), it can be seen that a delivery system of the present invention permits a controlled amount of the active (e.g., STP) to be released over a longer period of time, as compared to a gum composition where the active is free. In contrast, in the gum where the active is free, a high concentration of the active is initially delivered, followed by no active, which is undesirable. The delivery systems of the present invention enhance the uniformity of the active's release, and prolong its release in a controlled manner.

Example 5

Evaluation of Stain Removal Efficacy of Chewing Gum Compositions Including Free Versus Encapsulated Active(s)

Chewing gums containing free and encapsulated STP were evaluated for their stain removal efficacy. In particular, the chewing gum compositions were tested for their ability to remove stains on eight enamel pieces. The mean values are shown in Table 6 below. The experiment was conducted using a modification of the laboratory methods developed by Kleber, C J et al; A mastication device designed for the evaluation of chewing gums, J Dent Res. 60 (11); 109-114, November 1981. The amount of stain on the teeth before and after treatment was measured quantitatively using a colorimeter. In preparation for treatment, the baseline L*a*b* stain scores of the tooth specimens were determined and used to stratify the teeth into balanced groups of 8 specimens each. A mechanical instrument with a flow system to simulate the human mastication was used to treat the tooth specimens with the test chewing gum. For testing, a specimen block with an enamel squares was placed in both the upper and lower tooth holders of the instrument.

Artificial saliva (15 ml, pH 7.5) was placed in the reservoir. Approximately 1.5 grams of test chewing gum (i.e. 2 tablets) was placed between the repositioning paddles directly over the lower tooth specimen. Then the mastication motor was started and the two specimen blocks with the enamel squares were treated with the chewing gums for 10 minutes. This treatment procedure was repeated for 6 consecutive times (a total of 60 minutes of treatment. Fresh gums and artificial saliva were used for each 10-minute treatment period. Following the 6$^{th}$ treatment, the specimens were rinsed, allowed to dry for 30 minutes, and color readings made.

Stain Measurement

The color of the extrinsic stain on the bovine teeth was measured by taking diffuse reflectance absorbance readings with a Minolta spectrophotometer[8]. Absorbance measurement over the entire visible color spectrum were obtained using the CIELAB color scale. This scale quantifies color according to a 3 parameters, L* (lightness-darkness scale), a* (red-green chroma), and b* (yellow-blue chroma). In order to obtain reproducible readings, the stained enamel specimens were allowed to air-dry at room temperature for 30 minutes before measurements were made. Measurements were conducted by aligning the center of the 4-mm square segment of stained enamel directly over the 3-mm-diameter targeting aperture of the Minolta spectrophotometer. An average of 3 absorbance readings using the L*a*b* scale were taken for each specimen.

Stain Calculations

The overall change in the color of the stained teeth was calculated using the CIELAB equation $\Delta E=[(\Delta L^*)^2+(\Delta a^*)^2+(\Delta b^*)^2]^{1/2}$. The individual components of the L*a*b* scale represent the specific changes in the whiteness (L*), red-green color (a*), and yellow-blue color (b*). The ΔE value summarizes the overall change for each color factor (ΔL*, Δa*, and Δb*) and represents the ability of the test chewing gum to remove stain and whiten teeth. The data were calculated and defined as follows: Stain Removed=ΔE score after treatment (Table 6 below).

TABLE 6

Stain Removal Efficacy of Chewing Gums Including Free Versus Encapsulated Active(s)

| Prototype | ΔE |
|---|---|
| Free STP 0.5% | 2.4 |
| Encapsulated STP 0.5% (from Example 1) | 3.6 |
| Free Sodium Stearate 0.5%, STP 0.5%, (from Example 2) | 4.3 |
| Encapsulated Sodium stearate 0.5%, STP 0.5% | 5.1 |

As shown in Table 6, a chewing gum composition including encapsulated STP (from Example 1), changed the color of the stained teeth by a greater amount than the same gum composition including free STP. Moreover, a chewing gum composition including encapsulated sodium stearate and STP (from Example 2) changed the color of the stained teeth by a greater amount than the same gum composition including free sodium stearate and STP.

Example 6

Encapsulation of Enzymes

The delivery systems of Example 6 are directed to encapsulation of glucose oxidase, either alone (Table 7) or in combination with other actives (Table 8). The delivery system components are shown below in Tables 7 and 8.

In the delivery systems of the present example, glucose oxidase is first encapsulated in gum Arabic. This is done in an effort to provide the heat-labile enzyme with a protective coating prior to its encapsulation in polyvinyl acetate. For example, the glucose oxidase may be spray coated onto suspended enzyme particles in a fluidized air stream. A gum arabic coating may then be sprayed onto the suspended enzyme particles. Thereafter, the coated enzyme particles may be encapsulated in polyvinyl acetate, alone or in combination with other actives. In the delivery systems of the present example, glucose is an enzyme activator. The reaction of glucose with glucose oxidase results in the production of a peroxide. Sucralose, where present, serves as a taste masking agent.

TABLE 7

Encapsulation of Glucose Oxidase (GO)

| Components | Wt. Percent |
|---|---|
| Glucose oxidase (encapsulated w/gum Arabic, 30% GO) | 3.00 |
| Glucose | 4.00 |
| Hydrogenated Oil | 3.00 |
| Silicon dioxide | 30.00 |
| PVAc | 60.00 |
| Total | 100 |

TABLE 8

Encapsulation of Glucose Oxidase with Taste Masking Active

| Components | Wt. Percent |
|---|---|
| Glucose oxidase (encapsulated w/gum Arabic, 30% GO) | 4.00 |
| Glucose | 4.00 |
| Fat | 3.00 |
| Silicon dioxide | 23.00 |
| PVAc | 60.00 |
| Sucralose | 6.00 |
| Total | 100 |

The delivery systems of the present example are prepared as follows: PVAc is melted at about 85° C. in a high shear mixer. The hydrogenated oil (fat) is then added to the molten PVAc. The remaining components, including the coated enzyme particles, are added to the resulting mixture and mixed under high shear to completely disperse the components. The resulting filled polymer melt is cooled and ground to a particle size of less than 590 microns, and the encapsulated active(s) matrix is stored as described in Example 1.

Example 7

Chewing Gum Compositions Including Encapsulated Glucose Oxidase

A chewing gum composition is prepared using the encapsulated glucose oxidase prepared in Example 6 (Tables 7 or 8). The chewing gum components are shown in Table 9 below.

TABLE 9

Chewing Gum Composition

| Components | Wt. Percent |
| --- | --- |
| Gum Base | 39.0 |
| Sorbitol | QS |
| Mannitol | 9.00 |
| Flavor | 4.67 |
| Glycerin | 1.5 |
| Lecithin | 0.2 |
| Encapsulated Glucose Oxidase | 2.0 |
| Total | 100 |

The chewing gum composition is prepared as follows. The gum base is melted at a suitable temperature in a mixer. The remaining ingredients are then added to the melted gum base and mixed until the ingredients are completely dispersed. The resulting chewing gum composition is sized.

Example 8

Encapsulation of Surfactants

The delivery systems of Example 8 are directed to encapsulation of a surfactant (e.g., sodium stearate), either alone (Table 10) or in combination with other actives (Tables 11 and 12). The delivery system components are shown below in Tables 10-12. Sucralose serves as a taste masking active.

TABLE 10

Encapsulation of Sodium Stearate

| Components | Wt. Percent |
| --- | --- |
| Sodium stearate | 20 |
| Filler | 20 |
| PVAc | 60 |
| Total | 100 |

TABLE 11

Encapsulation of Sodium Stearate with Taste Masking Active

| Components | Wt. Percent |
| --- | --- |
| Sodium stearate | 30 |
| Talc | 8 |
| PVAc | 56 |
| Sucralose | 6 |
| Total | 100 |

TABLE 12

Encapsulation of Combination of Actives With Taste Masking Active

| Components | Wt. Percent |
| --- | --- |
| Sodium stearate | 10 |
| Sodium tripolyphosphate (STP) | 10 |
| Silicon dioxide | 14 |
| PVAc | 60 |
| Sucralose | 6 |
| Total | 100 |

The delivery systems of the present invention are prepared as follows: PVAc is melted as described above in Example 1. The remaining components of the delivery systems of Table 10, 11, or 12 are added to the molten PVAc and mixed under high shear. The resulting filled polymer melt is cooled and ground to a particle size of less than 590 microns, and the encapsulated active(s) matrix is stored as described in Example 1.

Example 8A

Chewing Gum Compositions Including Encapsulated Sodium Stearate

A chewing gum composition is prepared using the encapsulated sodium stearate prepared in Example 8 (Table 10, 11 or 12). The chewing gum components are shown in Table 13 below.

TABLE 13

Chewing Gum Composition

| Components | Wt. Percent |
| --- | --- |
| Gum Base | 39.0 |
| Sorbitol | QS |
| Mannitol | 9.0 |
| Flavor | 4.67 |
| Glycerin | 1.5 |
| Lecithin | 0.2 |
| Encapsulated Sodium Stearate | 5.0 |
| Total | 100 |

The chewing gum composition is prepared as follows. The gum base is melted at a suitable temperature in a mixer. The remaining ingredients are then added to the melted gum base and mixed until the ingredients are completely dispersed. The resulting chewing gum composition is sized.

Example 9

Encapsulation of Peroxides

In the present example, carbamide peroxide, either alone (Table 15) or in combination with dicalcium phosphate (Table 14) is encapsulated using a spray coating of fluidized particles of PVA.

TABLE 14

Encapsulation of Carbamide Peroxide and Dicalcium Phosphate

| Components | Wet Percent | Dry Percent |
|---|---|---|
| Center Cores | | |
| Carbamide Peroxide | 22.8 | 50 |
| Dicalcium phosphate | 9.0 | 20 |
| Coating Solution | | |
| Toluene | 54.5 | |
| Polyvinyl acetate | 13.6 | 30 |
| | 100 | 100 |

TABLE 15

Encapsulation of Carbamide Peroxide

| Components | Wet Percent | Dry Percent |
|---|---|---|
| Center Cores | | |
| Carbamide Peroxide | 18.24 | 40 |
| STP | 9.0 | 20 |
| Sucralose | 4.66 | 10 |
| Coating Solution | | |
| Toluene | 54.5 | |
| Polyvinyl acetate | 13.6 | 30 |
| | 100 | 100 |

The procedure used to prepare the delivery systems in the present example is as follows: The Wurster process is used to encapsulate carbamide peroxide, either alone (Table 15) or in combination with dicalcium phosphate (Table 14). Coating solutions are prepared using the compositions in Table 14 or 15 by stirring toluene and polyvinylacetate at 35° C. for 2 hrs. Carbamide peroxide/Dicalcium phosphate powders are suspended in a fluidizing air stream, which provides a generally cyclic flow in front of a spray nozzle. The spray nozzle sprays an atomized flow of coating solution for 240 minutes. The coated particles are then dried in the fluidized chamber for 50 minutes and stored below 35° C. under dry conditions.

Example 10

Chewing Gum Compositions Including Encapsulated Carbamide Peroxide

A chewing gum composition is prepared using encapsulated carbamide peroxide prepared in Example 9 (Table 14 or 15). The chewing gum components are shown in Table 16 below.

TABLE 16

Chewing Gum Compositions

| Components | Wt. Percent |
|---|---|
| Gum Base | 39.0 |
| Sorbitol | QS |
| Mannitol | 9.0 |
| Flavor | 4.67 |
| Glycerin | 1.5 |
| Lecithin | 0.2 |
| Encapsulated Carbamide Peroxide | 6.0 |
| Total | 100 |

The chewing gum composition is prepared as follows. The gum base is melted at a suitable temperature in a mixer. The remaining components are then added to the melted gum base and mixed until the components are completely dispersed. The resulting chewing gum composition is sized.

Example 11

Encapsulation of Calcium Casein Peptone-Calcium Phosphate CCP-CP (Recaldent)

Example 11 is directed to the encapsulation of a dental remineralization agent (i.e., recaldent), either alone (Table 17) or in combination with other actives (Table 18). As shown in Table 18, the recaldent can be combined with other actives, such as an anticaries agent (e.g., sodium fluoride), an anticalculus agent (e.g., STP), and a taste masking agent (e.g., sucralose). Taste masking agents are useful in masking bitter and/or metal tastes, such as those that may be associated with anticalculus agents, such as phosphate salts, etc.

TABLE 17

| Components | Wt. Percent |
|---|---|
| Recaldent | 29 |
| Hydrogenated Oil | 3 |
| Talc | 7 |
| PVAc | 61 |

TABLE 18

Combination of Actives with Taste Masking Active

| Components | Wt. Percent |
|---|---|
| Recaldent | 20 |
| Sodium Fluoride | 1 |
| Sodium tripolyphosphate (STP) | 17 |
| Hydrogenated Oil | 3 |
| Sucralose | 6 |
| PVAc | 53 |

The delivery systems shown in Tables 17 and 18 are prepared using similar methods to the method described in Example 1.

Example 12

Chewing Gum Compositions Including Encapsulated Recaldent

Chewing gum compositions are prepared using encapsulated recaldent prepared in Example 11 (Table 17 or 18). The chewing gum components are shown in Table 19.

TABLE 19

Chewing Gum compositions

| Components | Wt. Percent |
| --- | --- |
| Gum Base | 39.0 |
| Sorbitol | QS |
| Mannitol | 9.0 |
| Flavor | 10.00 |
| Glycerin | 1.5 |
| Lecitin | 0.2 |
| Encapsulated Recaldent | 5.0 |
| Total | 100 |

The chewing gum compositions are prepared as follows. The gum base is melted at a suitable temperature in a mixer. The remaining components are then added to the melted gum base and mixed until the components are completely dispersed. The resulting chewing gum compositions are sized.

Example 13

Encapsulation of Breath Freshening Agents

Example 13 is directed to the encapsulation of a breath freshening agent (chlorophyll), either alone (Table 20), or in combination with other actives (Tables 21 and 22). In the delivery system composition of Table 21, chlorophyll is encapsulated with sucralose, which may serve as both a sweetener and a taste masking agent. Moreover, in the delivery system composition of Table 22, chlorophyll and menthol-cyclodextrin each serve as breath freshening agents, which are encapsulated along with sucralose (a taste masking agent/sweetener) in the PVAc polymer matrix.

TABLE 20

Encapsulation of Chlorophyll

| Components | Wt. Percent |
| --- | --- |
| Chlorophyll | 40 |
| PVAc | 60 |

TABLE 21

Encapsulation of Chlorophyll with Taste Masking Active

| Components | Wt. Percent |
| --- | --- |
| Chlorophyll | 34 |
| PVAc | 60 |
| Sucralose | 6 |

TABLE 22

Encapsulation of Combination of Actives with Taste Masking Active

| Components | Wt. Percent |
| --- | --- |
| Chlorophyll | 27 |
| Menthol-cyclodextrin complex | 7 |
| Sucralose | 6 |
| PVAc | 60 |

The delivery system compositions in the present example are prepared by melting PVAc at a temperature of about 105° C. in a high shear mixer. The remaining components are then added and mixed under high shear. The resulting filled polymer melt is cooled and ground as described in Example 1, and the encapsulated active(s) matrix is stored in air tight containers with low humidity below 35° C.

Example 14

Chewing Gum Compositions Including Encapsulated Chlorophyll Compositions

Chewing gum compositions are prepared using encapsulated chlorophyll compositions prepared in Example 13 (compositions of Tables 20, 21 or 22). The chewing gum components are shown in Table 23

TABLE 23

Chewing Gum Compositions

| Components | Wt. Percent |
| --- | --- |
| Gum Base | 39.0 |
| Sorbitol | QS |
| Mannitol | 9.0 |
| Flavor | 4.67 |
| Glycerin | 1.5 |
| Lecithin | 0.2 |
| Encapsulated Chlorophyll | 5.0 |
| Total | 100 |

The chewing gum composition is prepared as follows. The gum base is melted at a suitable temperature in a mixer. The remaining components are then added to the melted gum base and mixed until the components are completely dispersed. The resulting chewing gum composition is sized.

Example 15

Encapsulation of Agents to Counter Breath Odor

Example 15 is directed to the encapsulation of an agent to counter breath odor (e.g., zinc citrate), either alone (Table 24) or in combination with other active agents (Tables 24A and 25). In the delivery system composition of Table 24A, zinc citrate is encapsulated along with an anticalculus agent (e.g., STP) and a taste masking agent/sweetener (e.g., sucralose). In the delivery system composition of Table 25, zinc citrate is encapsulated along with an anticalculus agent (e.g., STP), a surfactant (e.g., sodium stearate) and a taste masking agent/sweetener (e.g., sucralose).

TABLE 24

Encapsulation of Zinc Citrate

| Components | Wt. Percent |
| --- | --- |
| Zinc citrate | 40 |
| PVAc | 60 |

TABLE 24A

Encapsulation of Combination of Actives with Taste Masking Active

| Components | Wt. Percent |
| --- | --- |
| Zinc citrate | 7 |
| Sodium tripolyphosphate (STP) | 27 |
| PVAc | 60 |
| Sucralose | 6 |

TABLE 25

Encapsulation of Combination of Actives with Taste Masking Active

| Components | Wt. Percent |
| --- | --- |
| Zinc citrate | 10 |
| Sodium tripolyphosphate (STP) | 17 |
| Sucralose | 3 |
| Sodium stearate | 10 |
| PVAc | 60 |

The delivery system compositions are prepared as described above in Example 13.

Example 16

Chewing Gum Compositions Including Encapsulated Zinc Citrate

Chewing gum compositions are prepared using encapsulated zinc citrate prepared in Example 15 (Tables 24, 24A or 25). The chewing gum components are shown in Table 26.

TABLE 26

Chewing Gum Compositions

| Components | Wt. Percent |
| --- | --- |
| Gum Base | 39.0 |
| Sorbitol | QS |
| Mannitol | 9.0 |
| Flavor | 4.67 |
| Glycerin | 1.5 |
| Lecithin | 0.2 |
| Encapsulated zinc citrate | 5.0 |
| Total | 100 |

The chewing gum composition is prepared as follows. The gum base is melted at a suitable temperature in a mixer. The remaining components are then added to the melted gum base and mixed until the components are completely dispersed. The resulting chewing gum composition is sized.

Example 17

Encapsulation of Desensitizing Agent

Example 17 is directed to the encapsulation of a desensitizing agent (e.g., potassium nitrate), either alone (Table 27) or in combination with other actives (Tables 28 and 29). In the delivery system composition of Table 28, potassium nitrate is encapsulated along with sucralose (a sweetener/taste masking agent). Furthermore, in the delivery system composition of Table 29, potassium nitrate is encapsulated along with STP (an anticalculus agent) and sucralose (sweetener/taste masking agent).

TABLE 27

Encapsulation of Potassium Nitrate

| Components | Wt. Percent |
| --- | --- |
| Potassium nitrate | 40 |
| PVAc | 60 |

TABLE 28

Encapsulation of Potassium Nitrate with a Taste Masking Active

| Components | Wt. Percent |
| --- | --- |
| Potassium nitrate | 38 |
| PVAc | 60 |
| Sucralose | 2 |

TABLE 29

Encapsulation of Combination of Actives with a Taste Masking Active

| Components | Wt. Percent |
| --- | --- |
| Potassium nitrate | 17 |
| Sodium tripolyphosphate (STP) | 16 |
| PVAc | 60 |
| Sucralose | 7 |

The delivery system compositions are prepared as described above in Example 13.

Example 18

Chewing Gum Compositions Including Encapsulated Potassium Nitrate

Chewing gum compositions are prepared using encapsulated potassium nitrate prepared in Example 17 (Tables 27, 28 or 29). The chewing gum components are shown in Table 30.

TABLE 30

Chewing Gum Compositions

| Components | Wt. Percent |
| --- | --- |
| Gum base | 39.0 |
| Sorbitol | QS |
| Mannitol | 9.0 |
| Flavor | 4.67 |
| Glycerin | 1.5 |
| Lecithin | 0.2 |
| Encapsulated Potassium Nitrate | 3.0 |
| Total | 100 |

The chewing gum compositions are prepared as follows. The gum base is melted at a suitable temperature in a mixer. The remaining components are then added to the melted gum base and mixed until the components are completely dispersed. The resulting chewing gum composition is sized.

Examples 18 to 31 (Tables 3-44) below are directed to further oral delivery systems of the present invention. In Examples 18 to 31, a single active component is at least partially encapsulated in a PVAc matrix using extrusion. The active is encapsulated along with a plasticizer (hydrogenated oil) and an emulsifier (glycerol monostearate). Examples 32-43 (Tables 45-56) are directed to gum compositions including these delivery systems.

Example 18

Encapsulation of Sodium Tripolyphosphate

TABLE 31

| Components | Wt. Percent |
|---|---|
| Polyvinyl Acetate | 55.00 |
| Hydrogenated Oil | 3.75 |
| Glycerol Monostearate | 1.25 |
| Sodium tripolyphosphate | 40.00 |
| Total | 100 |

Procedure: Polyvinyl acetate is melted at a temperature of about 110° C. in a high shear mixer such as extruder (single or twin screw) or sigma or Banbury mixer. The hydrogenated oil and Glycerol monostearate are then added to the molten polyvinylacetate. STP is then added to the resulting mixture and mixed under high shear to completely disperse the ingredients. The resulting filled polymer melt is cooled and ground to particle size of less than 420 microns. The encapsulated matrix is stored in air tight containers with low humidity below 35° C.

Example 19

Encapsulation of Sodium Fluoride (NaF)

TABLE 32

| Components | Wt. Percent |
|---|---|
| Polyvinyl Acetate | 65.00 |
| Hydrogenated Oil | 3.75 |
| Glycerol Monostearate | 1.25 |
| Sodium Fluoride | 30.00 |
| Total | 100 |

Procedure: Polyvinyl acetate is melted at a temperature of about 110° C. in a high shear mixer such as extruder (single or twin screw) or sigma or Banbury mixer. The hydrogenated oil and Glycerol monostearate are then added to the molten polyvinyl acetate. NaF is then added to the resulting mixture and mixed under high shear to completely disperse the ingredients. The resulting filled polymer melt is cooled and ground to particle size of less than 420 microns. The encapsulated matrix is stored in air tight containers with low humidity below 35° C.

Example 20

Encapsulation of Calcium Peroxide

TABLE 33

| Components | Wt. Percent |
|---|---|
| Polyvinyl Acetate | 55.00 |
| Hydrogenated Oil | 3.75 |
| Glycerol Monostearate | 1.25 |
| Calcium Peroxide | 40.00 |
| Total | 100 |

Procedure: Polyvinyl acetate is melted at a temperature of about 80° C. in a high shear mixer such as extruder (single or twin screw) or sigma or Banbury mixer. The hydrogenated oil and Glycerol monostearate are then added to the molten polyvinyl acetate. Calcium peroxide is then added to the resulting mixture and mixed under high shear to completely disperse the ingredients. The resulting filled polymer melt is cooled and ground to particle size of less than 420 microns. The encapsulated matrix is stored in air tight containers with low humidity below 35° C.

Example 21

Encapsulation of Zinc Chloride

TABLE 34

| Components | Wt. Percent |
|---|---|
| Polyvinyl Acetate | 65.00 |
| Hydrogenated Oil | 3.75 |
| Glycerol Monostearate | 1.25 |
| Zinc Chloride | 30.00 |
| Total | 100 |

Procedure: Polyvinyl acetate is melted at a temperature of about 110° C. in a high shear mixer such as extruder (single or twin screw) or sigma or Banbury mixer. The hydrogenated oil and Glycerol monostearate are then added to the molten polyvinyl acetate. zinc chloride is then added to the resulting mixture and mixed under high shear to completely disperse the ingredients. The resulting filled polymer melt is cooled and ground to particle size of less than 420 microns. The encapsulated matrix is stored in air tight containers with low humidity below 35° C.

Example 22

Encapsulation of Carbamide Peroxide

TABLE 35

| Components | Wt. Percent |
|---|---|
| Polyvinyl Acetate | 55.00 |
| Hydrogenated Oil | 3.75 |
| Glycerol Monostearate | 1.25 |
| Carbamide Peroxide | 40.00 |
| Total | 100 |

Procedure: Polyvinyl acetate is melted at a temperature of about 80° C. in a high shear mixer such as extruder (single or twin screw) or sigma or Banbury mixer. The hydrogenated oil and Glycerol monostearate are then added to the molten polyvinyl acetate. Carbamide peroxide is then added to the resulting mixture and mixed under high shear to completely disperse the ingredients. The resulting filled polymer melt is cooled and ground to particle size of less than 420 microns. The encapsulated matrix is stored in air tight containers with low humidity below 35° C.

Example 23

Encapsulation of Potassium Nitrate (KNO3)

TABLE 36

| Components | Wt. Percent |
| --- | --- |
| Polyvinyl Acetate | 55.00 |
| Hydrogenated Oil | 3.75 |
| Glycerol Monostearate | 1.25 |
| Potassium Nitrate | 40.00 |
| Total | 100 |

Procedure: Polyvinyl acetate is melted at a temperature of about 110° C. in a high shear mixer such as extruder (single or twin screw) or sigma or Banbury mixer. The hydrogenated oil and Glycerol monostearate are then added to the molten polyvinyl acetate. KNO3 is then added to the resulting mixture and mixed under high shear to completely disperse the ingredients. The resulting filled polymer melt is cooled and ground to particle size of less than 420 microns. The encapsulated matrix is stored in air tight containers with low humidity below 35° C.

Example 24

Encapsulation of Chlorhexidine

TABLE 37

| Components | Wt. Percent |
| --- | --- |
| Polyvinyl Acetate | 55.00 |
| Hydrogenated Oil | 3.75 |
| Glycerol Monostearate | 1.25 |
| Chlorhexidine | 40.00 |
| Total | 100 |

Procedure: Polyvinyl acetate is melted at a temperature of about 80° C. in a high shear mixer such as extruder (single or twin screw) or sigma or Banbury mixer. The hydrogenated oil and Glycerol monostearate are then added to the molten polyvinyl acetate. Chlorhexidine is then added to the resulting mixture and mixed under high shear to completely disperse the ingredients. The resulting filled polymer melt is cooled and ground to particle size of less than 420 microns. The encapsulated matrix is stored in air tight containers with low humidity below 35° C.

Example 25

Encapsulation of Sodium Stearate

TABLE 38

| Components | Wt. Percent |
| --- | --- |
| Polyvinyl Acetate | 55.00 |
| Hydrogenated Oil | 3.75 |
| Glycerol Monostearate | 1.25 |
| Sodium stearate | 40.00 |
| Total | 100 |

Procedure: Polyvinyl acetate is melted at a temperature of about 110° C. in a high shear mixer such as extruder (single or twin screw) or sigma or Banbury mixer. The hydrogenated oil and Glycerol monostearate are then added to the molten polyvinyl acetate. Sodium stearate is then added to the resulting mixture and mixed under high shear to completely disperse the ingredients. The resulting filled polymer melt is cooled and ground to particle size of less than 420 microns. The encapsulated matrix is stored in air tight containers with low humidity below 35° C.

Example 26

Encapsulation of Sodium Bicarbonate

TABLE 39

| Components | Wt. Percent |
| --- | --- |
| Polyvinyl Acetate | 55.00 |
| Hydrogenated Oil | 3.75 |
| Glycerol Monostearate | 1.25 |
| Sodium Bicarbonate | 40.00 |
| Total | 100 |

Procedure: Polyvinyl acetate is melted at a temperature of about 110° C. in a high shear mixer such as extruder (single or twin screw) or sigma or Banbury mixer. The hydrogenated oil and Glycerol monostearate are then added to the molten polyvinyl acetate. NaHCO3 is then added to the resulting mixture and mixed under high shear to completely disperse the ingredients. The resulting filled polymer melt is cooled and ground to particle size of less than 420 microns. The encapsulated matrix is stored in air tight containers with low humidity below 35° C.

Example 27

Encapsulation of Cetylpyridinium Chloride (CPC)

TABLE 40

| Components | Wt. Percent |
| --- | --- |
| Polyvinyl Acetate | 55.00 |
| Hydrogenated Oil | 3.75 |
| Glycerol Monostearate | 1.25 |
| Cetylpyridinium chloride | 40.00 |
| Total | 100 |

Procedure: Polyvinyl acetate is melted at a temperature of about 80° C. in a high shear mixer such as extruder (single or twin screw) or sigma or Banbury mixer. The hydrogenated oil and Glycerol monostearate are then added to the molten polyvinyl acetate. CPC is then added to the resulting mixture and mixed under high shear to completely disperse the ingredients. The resulting filled polymer melt is cooled and ground to particle size of less than 420 microns. The encapsulated matrix is stored in air tight containers with low humidity below 35° C.

Example 28

Encapsulation of Calcium Casein Peptone-Calcium Phosphate CCP-CP (Recaldent)

TABLE 41

| Components | Wt. Percent |
|---|---|
| Polyvinyl Acetate | 55.00 |
| Hydrogenated Oil | 3.75 |
| Glycerol Monostearate | 1.25 |
| Recaldent | 40.00 |
| Total | 100 |

Procedure: Polyvinyl acetate is melted at a temperature of about 80° C. in a high shear mixer such as extruder (single or twin screw) or sigma or Banbury mixer. The hydrogenated oil and Glycerol monostearate are then added to the molten polyvinyl acetate. Recaldent is then added to the resulting mixture and mixed under high shear to completely disperse the ingredients. The resulting filled polymer melt is cooled and ground to particle size of less than 420 microns. The encapsulated matrix is stored in air tight containers with low humidity below 35° C.

Example 29

Encapsulation of Sodium Ricinoleate

TABLE 42

| Components | Wt. Percent |
|---|---|
| Polyvinyl Acetate | 55.00 |
| Hydrogenated Oil | 3.75 |
| Glycerol Monostearate | 1.25 |
| Sodium Ricinoleate | 40.00 |
| Total | 100 |

Procedure: Polyvinyl acetate is melted at a temperature of about 110° C. in a high shear mixer such as extruder (single or twin screw) or sigma or Banbury mixer. The hydrogenated oil and Glycerol monostearate are then added to the molten polyvinyl acetate. Sodium ricinoleate is then added to the resulting mixture and mixed under high shear to completely disperse the ingredients. The resulting filled polymer melt is cooled and ground to particle size of less than 420 microns. The encapsulated matrix is stored in air tight containers with low humidity below 35° C.

Example 30

Encapsulation of Sodium Hexametaphosphate (SHMP)

TABLE 43

| Components | Wt. Percent |
|---|---|
| Polyvinyl Acetate | 55.00 |
| Hydrogenated Oil | 3.75 |
| Glycerol Monostearate | 1.25 |
| Sodium Hexametaphosphate | 40.00 |
| Total | 100 |

Procedure: Polyvinyl acetate is melted at a temperature of about 110° C. in a high shear mixer such as extruder (single or twin screw) or sigma or Banbury mixer. The hydrogenated oil and Glycerol monostearate are then added to the molten polyvinyl acetate. SHMP is then added to the resulting mixture and mixed under high shear to completely disperse the ingredients. The resulting filled polymer melt is cooled and ground to particle size of less than 420 microns. The encapsulated matrix is stored in air tight containers with low humidity below 35° C.

Example 31

Encapsulation of Urea

TABLE 44

| Components | Wt. Percent |
|---|---|
| Polyvinyl Acetate | 55.00 |
| Hydrogenated Oil | 3.75 |
| Glycerol Monostearate | 1.25 |
| Urea | 40.00 |
| Total | 100 |

Procedure: Polyvinyl acetate is melted at a temperature of about 80° C. in a high shear mixer such as extruder (single or twin screw) or sigma or Banbury mixer. The hydrogenated oil and Glycerol monostearate are then added to the molten polyvinyl acetate. Urea is then added to the resulting mixture and mixed under high shear to completely disperse the ingredients. The resulting filled polymer melt is cooled and ground to particle size of less than 420 microns. The encapsulated matrix is stored in air tight containers with low humidity below 35° C.

Example 32

Chewing Gum Composition Including Encapsulated Sodium Tripolyphosphate (STP)

TABLE 45

| Components | Wt. Percent |
|---|---|
| Gum Base | 39.00 |
| Sorbitol | QS |
| Mannitol | 9.00 |
| Flavor | 3.67 |
| Glycerin | 1.50 |

TABLE 45-continued

| Components | Wt. Percent |
| --- | --- |
| Lecithin | 0.20 |
| Aspartame | 0.30 |
| AceK | 0.15 |
| Encapsulated STP (from Example 18) | 7.00 |
| Total | 100 |

Procedure: The chewing gum composition is prepared as follows. The gum base is melted at a suitable temperature in a mixer. The remaining components are then added to the melted gum base and mixed until the components are completely dispersed. The resulting chewing gum composition is sized.

Example 33

Chewing Gum Composition Including Encapsulated Sodium Fluoride (NaF)

TABLE 46

| Components | Wt. Percent |
| --- | --- |
| Gum Base | 39.00 |
| Sorbitol | QS |
| Mannitol | 9.00 |
| Flavor | 3.67 |
| Glycerin | 1.50 |
| Lecithin | 0.20 |
| Aspartame | 0.30 |
| AceK | 0.15 |
| Encapsulated NaF (from Example 19) | 0.40 |
| Total | 100 |

Procedure: The chewing gum composition is prepared as follows. The gum base is melted at a suitable temperature in a mixer. The remaining components are then added to the melted gum base and mixed until the components are completely dispersed. The resulting chewing gum composition is sized.

Example 34

Chewing Gum Composition Including Encapsulated Calcium Peroxide

TABLE 47

| Components | Wt. Percent |
| --- | --- |
| Gum Base | 39.00 |
| Sorbitol | QS |
| Mannitol | 9.00 |
| Flavor | 3.67 |
| Glycerin | 1.50 |
| Lecithin | 0.20 |
| Aspartame | 0.30 |
| AceK | 0.15 |
| Encapsulated Calcium peroxide (from Example 20) | 3.40 |
| Total | 100 |

Procedure: The chewing gum composition is prepared as follows. The gum base is melted at a suitable temperature in a mixer. The remaining components are then added to the melted gum base and mixed until the components are completely dispersed. The resulting chewing gum composition is sized.

Example 35

Chewing Gum Composition Including Encapsulated Zinc Chloride

TABLE 48

| Components | Wt. Percent |
| --- | --- |
| Gum Base | 39.00 |
| Sorbitol | QS |
| Mannitol | 9.00 |
| Flavor | 3.67 |
| Glycerin | 1.50 |
| Lecithin | 0.20 |
| Aspartame | 0.30 |
| AceK | 0.15 |
| Encapsulated Zinc chloride (from Example 21) | 1.10 |
| Total | 100 |

Procedure: The chewing gum composition is prepared as follows. The gum base is melted at a suitable temperature in a mixer. The remaining components are then added to the melted gum base and mixed until the components are completely dispersed. The resulting chewing gum composition is sized.

Example 36

Chewing Gum Composition Including Encapsulated Carbamide Peroxide

TABLE 49

| Components | Wt. Percent |
| --- | --- |
| Gum Base | 39.00 |
| Sorbitol | QS |
| Mannitol | 9.00 |
| Flavor | 3.67 |
| Glycerin | 1.50 |
| Lecithin | 0.20 |
| Aspartame | 0.30 |
| AceK | 0.15 |
| Encapsulated carbamide peroxide (from Example 22) | 3.00 |
| Total | 100 |

Procedure: The chewing gum composition is prepared as follows. The gum base is melted at a suitable temperature in a mixer. The remaining components are then added to the melted gum base and mixed until the components are completely dispersed. The resulting chewing gum composition is sized.

Example 37

Chewing Gum Composition Including Encapsulated Potassium Nitrate

TABLE 50

| Components | Wt. Percent |
|---|---|
| Gum Base | 39.00 |
| Sorbitol | QS |
| Mannitol | 9.00 |
| Flavor | 3.67 |
| Glycerin | 1.50 |
| Lecithin | 0.20 |
| Aspartame | 0.30 |
| AceK | 0.15 |
| Encapsulated Potassium Nitrate (from Example 23) | 6.00 |
| Total | 100 |

Procedure: The chewing gum composition is prepared as follows. The gum base is melted at a suitable temperature in a mixer. The remaining components are then added to the melted gum base and mixed until the components are completely dispersed. The resulting chewing gum composition is sized.

Example 38

Chewing Gum Composition Including Encapsulated Sodium Stearate

TABLE 51

| Components | Wt. Percent |
|---|---|
| Gum Base | 39.00 |
| Sorbitol | QS |
| Mannitol | 9.00 |
| Flavor | 3.67 |
| Glycerin | 1.50 |
| Lecithin | 0.20 |
| Aspartame | 0.30 |
| AceK | 0.15 |
| Encapsulated sodium stearate (from Example 25) | 3.00 |
| Total | 100 |

Procedure: The chewing gum composition is prepared as follows. The gum base is melted at a suitable temperature in a mixer. The remaining components are then added to the melted gum base and mixed until the components are completely dispersed. The resulting chewing gum composition is sized.

Example 39

Chewing Gum Composition Including Encapsulated Sodium Bicarbonate

TABLE 52

| Components | Wt. Percent |
|---|---|
| Gum Base | 39.00 |
| Sorbitol | QS |
| Mannitol | 9.00 |
| Flavor | 3.67 |
| Glycerin | 1.50 |
| Lecithin | 0.20 |
| Aspartame | 0.30 |
| AceK | 0.15 |
| Encapsulated sodium bicarbonate (from Example 26) | 4.00 |
| Total | 100 |

Procedure: The chewing gum composition is prepared as follows. The gum base is melted at a suitable temperature in a mixer. The remaining components are then added to the melted gum base and mixed until the components are completely dispersed. The resulting chewing gum composition is sized.

Example 40

Chewing Gum Composition Including Encapsulated Recaldent

TABLE 53

| Components | Wt. Percent |
|---|---|
| Gum Base | 39.00 |
| Sorbitol | QS |
| Mannitol | 9.00 |
| Flavor | 3.67 |
| Glycerin | 1.50 |
| Lecithin | 0.20 |
| Aspartame | 0.30 |
| AceK | 0.15 |
| Encapsulated Recaldent (from Example 28) | 4.00 |
| Total | 100 |

Procedure: The chewing gum composition is prepared as follows. The gum base is melted at a suitable temperature in a mixer. The remaining components are then added to the melted gum base and mixed until the components are completely dispersed. The resulting chewing gum composition is sized.

Example 41

Chewing Gum Composition Including Encapsulated Sodium Ricinoleate

TABLE 54

| Components | Wt. Percent |
| --- | --- |
| Gum Base | 39.00 |
| Sorbitol | QS |
| Mannitol | 9.00 |
| Flavor | 3.67 |
| Glycerin | 1.50 |
| Lecithin | 0.20 |
| Aspartame | 0.30 |
| AceK | 0.15 |
| Encapsulated sodium ricinoleate (from Example 29) | 2.00 |
| Total | 100 |

Procedure: The chewing gum composition is prepared as follows. The gum base is melted at a suitable temperature in a mixer. The remaining components are then added to the melted gum base and mixed until the components are completely dispersed. The resulting chewing gum composition is sized.

Example 42

Chewing Gum Composition Including Encapsulated Sodium Hexametaphosphate (SHMP)

TABLE 55

| Components | Wt. Percent |
| --- | --- |
| Gum Base | 39.00 |
| Sorbitol | QS |
| Mannitol | 9.00 |
| Flavor | 3.67 |
| Glycerin | 1.50 |
| Lecithin | 0.20 |
| Aspartame | 0.30 |
| AceK | 0.15 |
| Encapsulated SHMP (from Example 30) | 5.00 |
| Encapsulated sucralose | 0.90 |
| Total | 100 |

Procedure: The chewing gum composition is prepared as follows. The gum base is melted at a suitable temperature in a mixer. The remaining components are then added to the melted gum base and mixed until the components are completely dispersed. The resulting chewing gum composition is sized.

Example 43

Chewing Gum Composition Including Encapsulated Urea

TABLE 56

| Components | Wt. Percent |
| --- | --- |
| Gum Base | 39.00 |
| Sorbitol | QS |
| Mannitol | 9.00 |
| Flavor | 3.67 |
| Glycerin | 1.50 |
| Lecithin | 0.20 |
| Aspartame | 0.30 |
| AceK | 0.15 |
| Encapsulated Urea (from Example 31) | 5.00 |
| Total | 100 |

Procedure: The chewing gum composition is prepared as follows. The gum base is melted at a suitable temperature in a mixer. The remaining components are then added to the melted gum base and mixed until the components are completely dispersed. The resulting chewing gum composition is sized.

Examples 44-57 (Tables 57-70) below are directed to still further oral delivery systems of the present invention. In Examples 44-57, multiple active components are at least partially encapsulated in a PVAc matrix using extrusion. The actives are encapsulated, along with a plasticizer (hydrogenated oil) and an emulsifier (glycerol monostearate). Examples 58-71 (Tables 71-84) are directed to gum compositions including these delivery systems.

Example 44

Encapsulation of Sodium Tripolyphosphate (STP), Sodium Stearate and Sucralose

TABLE 57

| Components | Wt. Percent |
| --- | --- |
| Polyvinyl Acetate | 55.00 |
| Hydrogenated Oil | 3.75 |
| Glycerol Monostearate | 1.25 |
| Sodium tripolyphosphate | 20.00 |
| Sodium stearate | 10.00 |
| Sucralose | 10.00 |
| Total | 100 |

Procedure: Polyvinyl acetate is melted at a temperature of about 110° C. in a high shear mixer such as extruder (single or twin screw) or sigma or Banbury mixer. The hydrogenated oil and Glycerol monostearate are then added to the molten polyvinyl acetate. Actives are then added to the resulting mixture and mixed under high shear to completely disperse the ingredients. The resulting filled polymer melt is cooled and ground to particle size of less than 420 microns. The encapsulated matrix is stored in air tight containers with low humidity below 35° C.

Example 45

Encapsulation of Sodium Fluoride (NaF), STP and Sucralose

TABLE 58

| Components | Wt. Percent |
| --- | --- |
| Polyvinyl Acetate | 57.00 |
| Hydrogenated Oil | 3.75 |
| Glycerol Monostearate | 1.25 |
| Sodium tripolyphosphate | 25.00 |
| Sodium Fluoride | 3.00 |
| Sucralose | 10.00 |
| Total | 100 |

Procedure: Polyvinyl acetate is melted at a temperature of about 110° C. in a high shear mixer such as extruder (single or twin screw) or sigma or Banbury mixer. The hydrogenated oil and Glycerol monostearate are then added to the molten polyvinyl acetate. Actives are then added to the resulting mixture and mixed under high shear to completely disperse the ingredients. The resulting filled polymer melt is cooled and ground to particle size of less than 420 microns. The encapsulated matrix is stored in air tight containers with low humidity below 35° C.

Example 46

Encapsulation of Calcium Peroxide, SHMP and Sucralose

TABLE 59

| Components | Wt. Percent |
| --- | --- |
| Polyvinyl Acetate | 55.00 |
| Hydrogenated Oil | 3.75 |
| Glycerol Monostearate | 1.25 |
| Calcium Peroxide | 7.00 |
| Sodium hexametaphosphate | 23.00 |
| Sucralose | 10.00 |
| Total | 100 |

Procedure: Polyvinyl acetate is melted at a temperature of about 80° C. in a high shear mixer such as extruder (single or twin screw) or sigma or Banbury mixer. The hydrogenated oil and Glycerol monostearate are then added to the molten polyvinyl acetate. Actives are then added to the resulting mixture and mixed under high shear to completely disperse the ingredients. The resulting filled polymer melt is cooled and ground to particle size of less than 420 microns. The encapsulated matrix is stored in air tight containers with low humidity below 35° C.

Example 47

Encapsulation of Zinc Chloride, STP and Aspartame

TABLE 60

| Components | Wt. Percent |
| --- | --- |
| Polyvinyl Acetate | 55.00 |
| Hydrogenated Oil | 3.75 |
| Glycerol Monostearate | 1.25 |
| Zinc Chloride | 4.00 |
| Sodium tripolyphosphate | 26.00 |
| Aspartame | 10.00 |
| Total | 100 |

Procedure: Polyvinyl acetate is melted at a temperature of about 110° C. in a high shear mixer such as extruder (single or twin screw) or sigma or Banbury mixer. The hydrogenated oil and Glycerol monostearate are then added to the molten polyvinyl acetate. Actives are then added to the resulting mixture and mixed under high shear to completely disperse the ingredients. The resulting filled polymer melt is cooled and ground to particle size of less than 420 microns. The encapsulated matrix is stored in air tight containers with low humidity below 35° C.

Example 48

Encapsulation of Carbamide Peroxide, STP and Sucralose

TABLE 61

| Components | Wt. Percent |
| --- | --- |
| Polyvinyl Acetate | 55.00 |
| Hydrogenated Oil | 3.75 |
| Glycerol Monostearate | 1.25 |
| Sodium tripolyphosphate | 20.00 |
| Carbamide Peroxide | 10.00 |
| Sucralose | 10.00 |
| Total | 100 |

Procedure: Polyvinyl acetate is melted at a temperature of about 80° C. in a high shear mixer such as extruder (single or twin screw) or sigma or Banbury mixer. The hydrogenated oil and Glycerol monostearate are then added to the molten polyvinyl acetate. Actives are then added to the resulting mixture and mixed under high shear to completely disperse the ingredients. The resulting filled polymer melt is cooled and ground to particle size of less than 420 microns. The encapsulated matrix is stored in air tight containers with low humidity below 35° C.

Example 49

Encapsulation of Potassium Nitrate (KNO3), STP and Sucralose

TABLE 62

| Components | Wt. Percent |
|---|---|
| Polyvinyl Acetate | 55.00 |
| Hydrogenated Oil | 3.75 |
| Glycerol Monostearate | 1.25 |
| Potassium Nitrate | 10.00 |
| Sodium tripolyphosphate | 20.00 |
| Sucralose | 10.00 |
| Total | 100 |

Procedure: Polyvinyl acetate is melted at a temperature of about 110° C. in a high shear mixer such as extruder (single or twin screw) or sigma or Banbury mixer. The hydrogenated oil and Glycerol monostearate are then added to the molten polyvinyl acetate. Actives are then added to the resulting mixture and mixed under high shear to completely disperse the ingredients. The resulting filled polymer melt is cooled and ground to particle size of less than 420 microns. The encapsulated matrix is stored in air tight containers with low humidity below 35° C.

Example 50

Encapsulation of Chlorhexidine, STP, NaF and Aspartame

TABLE 63

| Components | Wt. Percent |
|---|---|
| Polyvinyl Acetate | 55.00 |
| Hydrogenated Oil | 3.75 |
| Glycerol Monostearate | 1.25 |
| Chlorhexidine | 4.00 |
| Sodium tripolyphosphate | 23.00 |
| Sodium Fluoride | 3.00 |
| Aspartame | 10.00 |
| Total | 100 |

Procedure: Polyvinyl acetate is melted at a temperature of about 80° C. in a high shear mixer such as extruder (single or twin screw) or sigma or Banbury mixer. The hydrogenated oil and Glycerol monostearate are then added to the molten polyvinyl acetate. Actives are then added to the resulting mixture and mixed under high shear to completely disperse the ingredients. The resulting filled polymer melt is cooled and ground to particle size of less than 420 microns. The encapsulated matrix is stored in air tight containers with low humidity below 35° C.

Example 51

Encapsulation of Sodium Stearate, STP, Menthol and Sucralose

TABLE 64

| Components | Wt. Percent |
|---|---|
| Polyvinyl Acetate | 55.00 |
| Hydrogenated Oil | 3.75 |
| Glycerol Monostearate | 1.25 |
| Sodium stearate | 4.00 |
| Sodium tripolyphosphate | 19.00 |
| Menthol | 7.00 |
| Sucralose | 10.00 |
| Total | 100 |

Procedure: Polyvinyl acetate is melted at a temperature of about 110° C. in a high shear mixer such as extruder (single or twin screw) or sigma or Banbury mixer. The hydrogenated oil and Glycerol monostearate are then added to the molten polyvinyl acetate. Actives are then added to the resulting mixture and mixed under high shear to completely disperse the ingredients. The resulting filled polymer melt is cooled and ground to particle size of less than 420 microns. The encapsulated matrix is stored in air tight containers with low humidity below 35° C.

Example 52

Encapsulation of Sodium Bicarbonate, STP, Sodium Stearate and Sucralose

TABLE 65

| Components | Wt. Percent |
|---|---|
| Polyvinyl Acetate | 55.00 |
| Hydrogenated Oil | 3.75 |
| Glycerol Monostearate | 1.25 |
| Sodium stearate | 4.00 |
| Sodium tripolyphosphate | 19.00 |
| Sodium bicarbonate | 7.00 |
| Sucralose | 10.00 |
| Total | 100 |

Procedure: Polyvinyl acetate is melted at a temperature of about 110° C. in a high shear mixer such as extruder (single or twin screw) or sigma or Banbury mixer. The hydrogenated oil and Glycerol monostearate are then added to the molten polyvinyl acetate. Actives are then added to the resulting mixture and mixed under high shear to completely disperse the ingredients. The resulting filled polymer melt is cooled and ground to particle size of less than 420 microns. The encapsulated matrix is stored in air tight containers with low humidity below 35° C.

Example 53

Encapsulation of Cetylpyridinium Chloride (CPC), NaF, STP and Sucralose

TABLE 66

| Components | Wt. Percent |
|---|---|
| Polyvinyl Acetate | 55.00 |
| Hydrogenated Oil | 3.75 |
| Glycerol Monostearate | 1.25 |
| Cetylpyridinium chloride | 4.00 |
| Sodium tripolyphosphate | 23.00 |
| Sodium Fluoride | 3.00 |
| Sucralose | 10.00 |
| Total | 100 |

Procedure: Polyvinyl acetate is melted at a temperature of about 80° C. in a high shear mixer such as extruder (single or twin screw) or sigma or Banbury mixer. The hydrogenated oil and Glycerol monostearate are then added to the molten polyvinyl acetate. Actives are then added to the resulting mixture and mixed under high shear to completely disperse the ingredients. The resulting filled polymer melt is cooled and ground to particle size of less than 420 microns. The encapsulated matrix is stored in air tight containers with low humidity below 35° C.

Example 54

Encapsulation of Calcium Casein Peptone-Calcium Phosphate CCP-CP (Recaldent), STP and Sucralose

TABLE 67

| Components | Wt. Percent |
|---|---|
| Polyvinyl Acetate | 55.00 |
| Hydrogenated Oil | 3.75 |
| Glycerol Monostearate | 1.25 |
| Recaldent | 10.00 |
| Sodium tripolyphosphate | 20.00 |
| Sucralose | 10.00 |
| Total | 100 |

Procedure: Polyvinyl acetate is melted at a temperature of about 80° C. in a high shear mixer such as extruder (single or twin screw) or sigma or Banbury mixer. The hydrogenated oil and Glycerol monostearate are then added to the molten polyvinyl acetate. Actives are then added to the resulting mixture and mixed under high shear to completely disperse the ingredients. The resulting filled polymer melt is cooled and ground to particle size of less than 420 microns. The encapsulated matrix is stored in air tight containers with low humidity below 35° C.

Example 55

Encapsulation of Sodium Ricinoleate, STP and Aspartame

TABLE 68

| Components | Wt. Percent |
|---|---|
| Polyvinyl Acetate | 55.00 |
| Hydrogenated Oil | 3.75 |
| Glycerol Monostearate | 1.25 |
| Sodium Ricinoleate | 4.00 |
| Sodium tripolyphosphate | 26.00 |
| Aspartame | 10.00 |
| Total | 100 |

Procedure: Polyvinyl acetate is melted at a temperature of about 110° C. in a high shear mixer such as extruder (single or twin screw) or sigma or Banbury mixer. The hydrogenated oil and Glycerol monostearate are then added to the molten polyvinyl acetate. Actives are then added to the resulting mixture and mixed under high shear to completely disperse the ingredients. The resulting filled polymer melt is cooled and ground to particle size of less than 420 microns. The encapsulated matrix is stored in air tight containers with low humidity below 35° C.

Example 56

Encapsulation of Sodium Hexametaphosphate (SHMP), Sodium Stearate and Sucralose

TABLE 69

| Components | Wt. Percent |
|---|---|
| Polyvinyl Acetate | 55.00 |
| Hydrogenated Oil | 3.75 |
| Glycerol Monostearate | 1.25 |
| Sodium Hexametaphosphate | 26.00 |
| Sodium stearate | 4.00 |
| Sucralose | 10.00 |
| Total | 100 |

Procedure: Polyvinyl acetate is melted at a temperature of about 110° C. in a high shear mixer such as extruder (single or twin screw) or sigma or Banbury mixer. The hydrogenated oil and Glycerol monostearate are then added to the molten polyvinyl acetate. SHMP is then added to the resulting mixture and mixed under high shear to completely disperse the ingredients. The resulting filled polymer melt is cooled and ground to particle size of less than 420 microns. The encapsulated matrix is stored in air tight containers with low humidity below 35° C.

Example 57

Encapsulation of Urea, STP and Sucralose

TABLE 70

| Components | Wt. Percent |
|---|---|
| Polyvinyl Acetate | 55.00 |
| Hydrogenated Oil | 3.75 |
| Glycerol Monostearate | 1.25 |
| Urea | 10.00 |
| Sodium tripolyphosphate | 20.00 |
| Sucralose | 10.00 |
| Total | 100 |

Procedure: Polyvinyl acetate is melted at a temperature of about 80° C. in a high shear mixer such as extruder (single or twin screw) or sigma or Banbury mixer. The hydrogenated oil and Glycerol monostearate are then added to the molten polyvinyl acetate. Actives are then added to the resulting mixture and mixed under high shear to completely disperse the ingredients. The resulting filled polymer melt is cooled and ground to particle size of less than 420 microns. The encapsulated matrix is stored in air tight containers with low humidity below 35° C.

Example 58

Chewing Gum Composition Including Encapsulated Sodium Tripolyphosphate (STP), Sodium Stearate and Sucralose

TABLE 71

| Components | Wt. Percent |
|---|---|
| Gum Base | 39.00 |
| Sorbitol | QS |
| Mannitol | 9.00 |
| Flavor | 3.67 |
| Glycerin | 1.50 |
| Lecithin | 0.20 |
| Aspartame | 0.30 |
| AceK | 0.15 |
| Encapsulated STP, Sodium stearate and sucralose (from Example 44) | 7.00 |
| Total | 100 |

Procedure: The chewing gum composition is prepared as follows. The gum base is melted at a suitable temperature in a mixer. The remaining components are then added to the melted gum base and mixed until the components are completely dispersed. The resulting chewing gum composition is sized.

Example 59

Chewing Gum Composition Including Encapsulated Sodium Fluoride (NaF), STP, and Sucralose

TABLE 72

| Components | Wt. Percent |
|---|---|
| Gum Base | 39.00 |
| Sorbitol | QS |
| Mannitol | 9.00 |
| Flavor | 3.67 |
| Glycerin | 1.50 |
| Lecithin | 0.20 |
| Aspartame | 0.30 |
| AceK | 0.15 |
| Encapsulated NaF, STP and sucralose (from Example 45) | 5.00 |
| Total | 100 |

Procedure: The chewing gum composition is prepared as follows. The gum base is melted at a suitable temperature in a mixer. The remaining components are then added to the melted gum base and mixed until the components are completely dispersed. The resulting chewing gum composition is sized.

Example 60

Chewing Gum Composition Including Encapsulated Calcium Peroxide, SHMP and Sucralose

TABLE 73

| Components | Wt. Percent |
|---|---|
| Gum Base | 39.00 |
| Sorbitol | QS |
| Mannitol | 9.00 |
| Flavor | 3.67 |
| Glycerin | 1.50 |
| Lecithin | 0.20 |
| Aspartame | 0.30 |
| AceK | 0.15 |
| Encapsulated Calcium peroxide, SHMP and sucralose (from Example 46) | 5.00 |
| Total | 100 |

Procedure: The chewing gum composition is prepared as follows. The gum base is melted at a suitable temperature in a mixer. The remaining components are then added to the melted gum base and mixed until the components are completely dispersed. The resulting chewing gum composition is sized.

Example 61

Chewing Gum Composition Including Encapsulated Zinc Chloride, STP and Aspartame

TABLE 74

| Components | Wt. Percent |
|---|---|
| Gum Base | 39.00 |
| Sorbitol | QS |
| Mannitol | 9.00 |
| Flavor | 3.67 |
| Glycerin | 1.50 |
| Lecithin | 0.20 |
| Aspartame | 0.30 |
| AceK | 0.15 |
| Encapsulated Zinc chloride, STP and aspartame (from Example 47) | 5.00 |
| Total | 100 |

Procedure: The chewing gum composition is prepared as follows. The gum base is melted at a suitable temperature in a mixer. The remaining components are then added to the melted gum base and mixed until the components are completely dispersed. The resulting chewing gum composition is sized.

Example 62

Chewing Gum Composition Including Encapsulated Carbamide Peroxide, STP and Sucralose

TABLE 75

| Components | Wt. Percent |
|---|---|
| Gum Base | 39.00 |
| Sorbitol | QS |
| Mannitol | 9.00 |
| Flavor | 3.67 |
| Glycerin | 1.50 |
| Lecithin | 0.20 |
| Aspartame | 0.30 |
| AceK | 0.15 |
| Encapsulated carbamide peroxide, STP and sucralose (from Example 48) | 3.00 |
| Total | 100 |

Procedure: The chewing gum composition is prepared as follows. The gum base is melted at a suitable temperature in a mixer. The remaining components are then added to the melted gum base and mixed until the components are completely dispersed. The resulting chewing gum composition is sized.

Example 63

Chewing Gum Composition Including Encapsulated Potassium Nitrate, STP and Sucralose

TABLE 76

| Components | Wt. Percent |
|---|---|
| Gum Base | 39.00 |
| Sorbitol | QS |
| Mannitol | 9.00 |
| Flavor | 3.67 |
| Glycerin | 1.50 |
| Lecithin | 0.20 |
| Aspartame | 0.30 |
| AceK | 0.15 |
| Encapsulated Potassium Nitrate and STP and sucralose (from Example 49) | 6.00 |
| Total | 100 |

Procedure: The chewing gum composition is prepared as follows. The gum base is melted at a suitable temperature in a mixer. The remaining components are then added to the melted gum base and mixed until the components are completely dispersed. The resulting chewing gum composition is sized.

Example 64

Chewing Gum Composition Including Encapsulated Chlorhexidine, STP, NaF and Aspartame

TABLE 77

| Components | Wt. Percent |
|---|---|
| Gum Base | 39.00 |
| Sorbitol | QS |
| Mannitol | 9.00 |
| Flavor | 3.67 |
| Glycerin | 1.50 |
| Lecithin | 0.20 |
| Aspartame | 0.30 |
| AceK | 0.15 |
| Encapsulated chlorehexidine, STP, NaF and aspartame (from Example 50) | 6.00 |
| Total | 100 |

Procedure: The chewing gum composition is prepared as follows. The gum base is melted at a suitable temperature in a mixer. The remaining components are then added to the melted gum base and mixed until the components are completely dispersed. The resulting chewing gum composition is sized.

Example 65

Chewing Gum Composition Including Encapsulated Sodium Stearate, Menthol, STP and Sucralose

TABLE 78

| Components | Wt. Percent |
| --- | --- |
| Gum Base | 39.00 |
| Sorbitol | QS |
| Mannitol | 9.00 |
| Flavor | 3.67 |
| Glycerin | 1.50 |
| Lecithin | 0.20 |
| Aspartame | 0.30 |
| AceK | 0.15 |
| Encapsulated sodium stearate, menthol, STP and sucralose (from Example 51) | 6.00 |
| Total | 100 |

Procedure: The chewing gum composition is prepared as follows. The gum base is melted at a suitable temperature in a mixer. The remaining components are then added to the melted gum base and mixed until the components are completely dispersed. The resulting chewing gum composition is sized.

Example 66

Chewing Gum Composition Including Encapsulated Sodium Bicarbonate, STP, Sodium Stearate and Sucralose

TABLE 79

| Components | Wt. Percent |
| --- | --- |
| Gum Base | 39.00 |
| Sorbitol | QS |
| Mannitol | 9.00 |
| Flavor | 3.67 |
| Glycerin | 1.50 |
| Lecithin | 0.20 |
| Aspartame | 0.30 |
| AceK | 0.15 |
| Encapsulated Sodium bicarbonate, STP, Sodium stearate and sucralose (from Example 52) | 6.00 |
| Total | 100 |

Procedure: The chewing gum composition is prepared as follows. The gum base is melted at a suitable temperature in a mixer. The remaining components are then added to the melted gum base and mixed until the components are completely dispersed. The resulting chewing gum composition is sized.

Example 67

Chewing Gum Composition Including Encapsulated Cetylpyridinium Chloride (CPC), NaF, STP and Sucralose

TABLE 80

| Components | Wt. Percent |
| --- | --- |
| Gum Base | 39.00 |
| Sorbitol | QS |
| Mannitol | 9.00 |
| Flavor | 3.67 |
| Glycerin | 1.50 |
| Lecithin | 0.20 |
| Aspartame | 0.30 |
| AceK | 0.15 |
| Encapsulated CPC, NaF, STP and sucralose (from Example 53) | 4.00 |
| Total | 100 |

Procedure: The chewing gum composition is prepared as follows. The gum base is melted at a suitable temperature in a mixer. The remaining components are then added to the melted gum base and mixed until the components are completely dispersed. The resulting chewing gum composition is sized.

Example 68

Chewing Gum Composition Including Encapsulated Recaldent, STP and Sucralose

TABLE 81

| Components | Wt. Percent |
| --- | --- |
| Gum Base | 39.00 |
| Sorbitol | QS |
| Mannitol | 9.00 |
| Flavor | 3.67 |
| Glycerin | 1.50 |
| Lecithin | 0.20 |
| Aspartame | 0.30 |
| AceK | 0.15 |
| Encapsulated Recaldent, STP and sucralose (from Example 54) | 4.00 |
| Total | 100.00 |

Procedure: The chewing gum composition is prepared as follows. The gum base is melted at a suitable temperature in a mixer. The remaining components are then added to the melted gum base and mixed until the components are completely dispersed. The resulting chewing gum composition is sized.

Example 69

Chewing Gum Composition Including Encapsulated Sodium Ricinoleate, STP and Aspartame

TABLE 82

| Components | Wt. Percent |
| --- | --- |
| Gum Base | 39.00 |
| Sorbitol | QS |
| Mannitol | 9.00 |
| Flavor | 3.67 |
| Glycerin | 1.50 |
| Lecithin | 0.20 |
| Aspartame | 0.30 |
| AceK | 0.15 |
| Encapsulated Sodium recinolate, STP and aspartame (from Example 55) | 4.00 |
| Total | 100 |

Procedure: The chewing gum composition is prepared as follows. The gum base is melted at a suitable temperature in a mixer. The remaining components are then added to the melted gum base and mixed until the components are completely dispersed. The resulting chewing gum composition is sized.

Example 70

Chewing Gum Composition Including Encapsulated Sodium Hexametaphosphate (SHMP), Sodium Stearate and Sucralose

TABLE 83

| Components | Wt. Percent |
| --- | --- |
| Gum Base | 39.00 |
| Sorbitol | QS |
| Mannitol | 9.00 |
| Flavor | 3.67 |
| Glycerin | 1.50 |
| Lecithin | 0.20 |
| Aspartame | 0.30 |
| AceK | 0.15 |
| Encapsulated SHMP, sodium stearate and sucralose (from Example 56) | 5.00 |
| Total | 100 |

Procedure: The chewing gum composition is prepared as follows. The gum base is melted at a suitable temperature in a mixer. The remaining components are then added to the melted gum base and mixed until the components are completely dispersed. The resulting chewing gum composition is sized.

Example 71

Chewing Gum Composition Containing Encapsulated Urea, STP and Sucralose

TABLE 84

| Components | Wt. Percent |
| --- | --- |
| Gum Base | 39.00 |
| Sorbitol | QS |
| Mannitol | 9.00 |
| Flavor | 3.67 |
| Glycerin | 1.50 |
| Lecithin | 0.20 |
| Aspartame | 0.30 |
| AceK | 0.15 |
| Encapsulated Urea, STP and sucralose (from Example 57) | 5.00 |
| Total | 100 |

Procedure: The chewing gum composition is prepared as follows. The gum base is melted at a suitable temperature in a mixer. The remaining components are then added to the melted gum base and mixed until the components are completely dispersed. The resulting chewing gum composition is sized.

What is claimed is:

1. An oral delivery system comprising:
   at least one active component; wherein the at least one active component is an anticalculus agent is selected from the group consisting of pyrophosphates, triphosphates, polyphosphates, polyphosphonates and combinations thereof; and
   a polymer matrix at least partially encapsulating said at least one active component, said polymer matrix having a tensile strength of at least 6,500 psi and comprising at least one polymer having a water absorption of about 0.1% to about 15% by weight as measurable by ASTM D570-98 and hydrogenated oil; wherein the polymer is selected from the group consisting of polyvinyl acetate, polyvinyl acetatephthalate, polymethylmethacrylate, polyethylene terephthalate and combinations thereof.

2. The system of claim 1, wherein the delivery system, when used in an oral composition, releases a controlled amount of the active component in an oral cavity over a longer period of time as compared to an oral composition wherein the active component is free.

3. The system of claim 2, wherein the period of time is about 5 to about 60 minutes.

4. The system of claim 3, wherein at least 50% of the active component remains in the oral composition after the time period of about 5 to about 60 minutes.

5. The system of claim 1, wherein the polymer matrix has a tensile strength of about 20,000 to about 50,000 psi.

6. The system of claim 1, wherein the anticalculus agent is sodium hexametaphosphate.

7. The system of claim 1, wherein the anticalculus agent is sodium tripolyphosphate.

8. An oral composition comprising the oral delivery system of claim 1.

9. The oral composition of claim 8, further comprising a carrier composition selected from the group consisting of a gum base, a confectionary base, a toothpaste base, a gel dentifrice base and a tooth powder base.

10. The oral composition of claim 9, wherein the composition is a gum composition.

11. A gum composition comprising:
(a) a gum base; and
(b) a delivery system, said delivery system comprising (i) at least one active component; and (ii) a polymer matrix at least partially encapsulating said at least one active component, said polymer matrix having a tensile strength of at least 6,500 psi and comprising at least one polymer having a water absorption of about 0.1% to about 15% by weight as measurable by ASTM D570-98 and hydrogenated oil; wherein the at least one active component is an anticalculus agent is selected from the group consisting of pyrophosphates, triphosphates, polyphosphates, polyphosphonates and combinations thereof; and wherein the polymer is selected from the group consisting of polyvinyl acetate, polyvinyl acetatephthalate, polymethylmethacrylate, polyethylene terephthalate and combinations thereof.

12. The gum composition of claim 11, wherein the polymer matrix has a tensile strength of about 20,000 to about 50,000 psi.

13. A method for preparing an oral delivery system, the method comprising:
at least partially encapsulating at least one active component, wherein the at least one active component is an anticalculus agent is selected from the group consisting of pyrophosphates, triphosphates, polyphosphates, polyphosphonates and combinations thereof in a polymer matrix, thereby forming an oral delivery system, said polymer matrix having a tensile strength of at least 6,500 psi and comprising at least one polymer having a water absorption of about 0.1% to about 15% by weight as measurable by ASTM D570-98 and hydrogenated oil; wherein the polymer is selected from the group consisting of polyvinyl acetate, polyvinyl acetatephthalate, polymethylmethacrylate, polyethylene terephthalate and combinations thereof.

14. The method of claim 13, wherein the polymer matrix has a tensile strength of about 20,000 to about 50,000 psi.

15. A method for preparing an oral composition comprising:
providing an oral delivery system, said system comprising (i) at least one active component; wherein the at least one active component is an anticalculus agent is selected from the group consisting of pyrophosphates, triphosphates, polyphosphates, polyphosphonates and combinations thereof; and (ii) a polymer matrix at least partially encapsulating said at least one active component, said polymer matrix having a tensile strength of at least 6,500 psi and comprising at least one polymer having a water absorption of about 0.1% to about 15% by weight as measurable by ASTM D570-98 and hydrogenated oil; wherein the polymer is selected from the group consisting of polyvinyl acetate, polyvinyl acetatephthalate, polymethylmethacrylate, polyethylene terephthalate and combinations thereof; and
combining the oral delivery system with a carrier composition.

16. The method of claim 15, wherein the carrier composition is selected from the group consisting of a gum base, a confectionary base, a toothpaste base, a gel dentifrice base and a tooth powder base.

17. A method for preparing a gum composition, the method comprising:
at least partially encapsulating at least one active component; wherein the at least one active component is an anticalculus agent is selected from the group consisting of pyrophosphates, triphosphates, polyphosphates, polyphosphonates and combinations thereof, in a polymer matrix, said polymer matrix having a tensile strength of at least about 6,500 psi and comprising at least one polymer having a water absorption of about 0.1% to about 15% by weight as measurable by ASTM D570-98 and hydrogenated oil; wherein the polymer is selected from the group consisting of polyvinyl acetate, polyvinyl acetatephthalate, polymethylmethacrylate, polyethylene terephthalate and combinations thereof;
heating a gum base to soften the base;
mixing the softened gum base with the at least partially encapsulated active component to obtain a substantially homogeneous mixture;
cooling the mixture; and
forming the cooled mixture into gum pieces.

18. A method of controlling the release of an active component from an oral delivery system comprising:
providing the oral delivery system of claim 1;
employing the oral delivery system in an oral cavity, whereby a controlled amount of the at least one active component is released into the oral cavity.

19. The method of claim 18, wherein the oral delivery system is present in a gum, the controlled amount of the at least one active component being released into the oral cavity upon mastication of the gum.

20. The oral delivery system of claim 1, which is made by melting the polymer in a mixer, adding a hydrogenated oil to the mixer, and adding the at least one active component to the mixer, mixing the polymer, the hydrogenated oil, and the at least one active component in the mixer to form a polymer matrix at least partially encapsulating the at least one active component.

21. The oral delivery system of claim 20, wherein the mixer is an extruder.

22. The system of claim 1 wherein the at least one active component is a dialkali metal pyrophosphate salt, a tetra alkali polyphosphate salt, or a combination thereof.

23. The system of claim 1 wherein the at least one active component is selected from the group consisting of tetrasodium pyrophosphate, sodium tripolyphosphate, sodium hexametaphosphate, and combinations thereof.

24. The system of claim 1, wherein said polymer is polyvinyl acetate.

25. The system of claim 1, wherein said system additionally contains a taste masking agent.

26. The system of claim 1, wherein the polymer matrix fully encapsulates the at least one active component.

* * * * *